US010626155B2

(12) United States Patent
Morisseau et al.

(10) Patent No.: US 10,626,155 B2
(45) Date of Patent: Apr. 21, 2020

(54) IL-15 AND IL-15R\ALPHA SUSHI DOMAIN BASED IMMUNOCYTOKINES

(71) Applicants: Cytune Pharma, Nantes (FR); INSERM (Institut National De La Sante Et De La Recherche Medicale), Paris (FR)

(72) Inventors: Sebastien Daniel Morisseau, Donges (FR); Geraldine Teppaz, Nantes (FR); Yannick Laurent Joseph Jacques, Nantes (FR); Bruno Gilbert Marc Robert, Valflaunes (FR); Guy Luc Michel De Martynoff, Mont-St-Guibert (BE); David Bechard, Saint Etienne de Montluc (FR)

(73) Assignees: Cytune Pharma, Nantes (FR); INSERM (Institut National De La Sante Et De La Recherche Medicale), Paris (FR)

( * ) Notice: Subject to any disclaimer, the term of this patent is extended or adjusted under 35 U.S.C. 154(b) by 123 days.

(21) Appl. No.: 15/214,032

(22) Filed: Jul. 19, 2016

(65) Prior Publication Data
US 2016/0318986 A1  Nov. 3, 2016

Related U.S. Application Data

(63) Continuation of application No. 14/129,188, filed as application No. PCT/EP2012/002650 on Jun. 22, 2012, now abandoned.

(30) Foreign Application Priority Data

Jun. 24, 2011  (EP) .................... 11358005

(51) Int. Cl.
| | |
|---|---|
| *C07K 14/54* | (2006.01) |
| *A61K 38/20* | (2006.01) |
| *C07K 14/715* | (2006.01) |
| *A61K 38/00* | (2006.01) |
| *C07K 16/28* | (2006.01) |
| *C07K 16/30* | (2006.01) |
| *C07K 16/32* | (2006.01) |
| *A61K 39/00* | (2006.01) |

(52) U.S. Cl.
CPC ...... *C07K 14/5443* (2013.01); *A61K 38/2086* (2013.01); *C07K 14/7155* (2013.01); *C07K 16/2887* (2013.01); *C07K 16/3084* (2013.01); *C07K 16/32* (2013.01); *A61K 38/00* (2013.01); *A61K 2039/505* (2013.01); *C07K 2317/24* (2013.01); *C07K 2317/51* (2013.01); *C07K 2317/515* (2013.01); *C07K 2317/622* (2013.01); *C07K 2319/00* (2013.01); *C07K 2319/31* (2013.01); *C07K 2319/32* (2013.01); *C07K 2319/33* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 4,671,958 A | 6/1987 | Rodwell et al. | |
| 5,073,627 A | 12/1991 | Curtis et al. | |
| 5,108,910 A | 4/1992 | Curtis et al. | |
| 5,225,539 A | 7/1993 | Winter | |
| 5,314,995 A | 5/1994 | Fell et al. | |
| 5,558,864 A | 9/1996 | Bendig et al. | |
| 5,585,089 A | 12/1996 | Queen et al. | |
| 5,595,721 A | 1/1997 | Kaminski et al. | |
| 5,645,835 A | 7/1997 | Fell, Jr. et al. | |
| 5,677,171 A | 10/1997 | Hudziak et al. | |
| 5,730,969 A | 3/1998 | Hora et al. | |
| 5,736,137 A | 4/1998 | Anderson et al. | |
| 5,776,456 A | 7/1998 | Anderson et al. | |
| 5,821,337 A | 10/1998 | Carter et al. | |
| 6,235,883 B1 | 5/2001 | Jakobovits et al. | |
| 6,803,192 B1 | 10/2004 | Chen | |
| 6,808,710 B1 | 10/2004 | Wood et al. | |
| 6,936,704 B1 | 8/2005 | Freeman et al. | |
| 7,060,808 B1 | 6/2006 | Goldstein et al. | |
| 7,888,071 B2 | 2/2011 | Gillies et al. | |
| 7,906,118 B2 | 3/2011 | Chang et al. | |
| 8,124,084 B2 | 2/2012 | Lefrancois et al. | |
| 8,287,865 B2 | 10/2012 | Hansen et al. | |

(Continued)

FOREIGN PATENT DOCUMENTS

| | | |
|---|---|---|
| CN | 1599867 | 3/2005 |
| EP | 0305967 | 3/1989 |

(Continued)

OTHER PUBLICATIONS

Bowie et al. (Science, 1990, 247:1306-1310) (Year: 1990).*

(Continued)

*Primary Examiner* — Brian Gangle
*Assistant Examiner* — Andrea K McCollum
(74) *Attorney, Agent, or Firm* — Kagan Binder, PLLC

(57) ABSTRACT

The present invention relates to an immunocytokine comprising (a) a conjugate, and (b) an antibody or a fragment thereof directly or indirectly linked by covalence to said conjugate, wherein said conjugate comprises (i) a polypeptide comprising the amino acid sequence of the interleukin 15 or derivatives thereof, and (ii) a polypeptide comprising the amino acid sequence of the sushi domain of the interleukin 15R alpha (IL-15Rα) or derivatives thereof; and uses thereof.

8 Claims, 12 Drawing Sheets
Specification includes a Sequence Listing.

(56) References Cited

U.S. PATENT DOCUMENTS

| | | | |
|---|---|---|---|
| 8,951,524 | B2 | 2/2015 | Birkle et al. |
| 8,981,063 | B2 | 3/2015 | Chen |
| 2006/0025885 | A1 | 2/2006 | Steffl et al. |
| 2009/0238791 | A1* | 9/2009 | Jacques .............. C07K 14/5443 424/85.2 |
| 2010/0150910 | A1 | 6/2010 | Birkle et al. |
| 2011/0177074 | A1 | 7/2011 | Sivakumar et al. |
| 2012/0244118 | A1 | 9/2012 | Berraondo Lopez et al. |
| 2012/0276125 | A1 | 11/2012 | Ast et al. |

FOREIGN PATENT DOCUMENTS

| | | |
|---|---|---|
| GB | 2188638 | 10/1987 |
| WO | 85/00974 | 3/1985 |
| WO | 86/01533 A1 | 3/1986 |
| WO | 92/15683 A1 | 9/1992 |
| WO | 95/27722 | 10/1995 |
| WO | 2000/047228 A1 | 8/2000 |
| WO | 2001/058957 A2 | 8/2001 |
| WO | 2002/072605 A2 | 9/2002 |
| WO | 2003/078334 A1 | 9/2003 |
| WO | 2004/035607 | 4/2004 |
| WO | 2005/085282 A1 | 9/2005 |
| WO | 2007/001677 | 1/2007 |
| WO | 2007/046006 A2 | 4/2007 |
| WO | 2007/084342 | 7/2007 |
| WO | 2007/128563 | 11/2007 |
| WO | 2008/043777 A1 | 4/2008 |
| WO | 2008/143794 A1 | 11/2008 |
| WO | 2009/002562 A2 | 12/2008 |
| WO | 2009/012600 A1 | 1/2009 |
| WO | 2009/135031 | 11/2009 |
| WO | 2011/070214 A2 | 6/2011 |
| WO | 2012/175222 | 12/2012 |
| WO | 2012/178137 | 12/2012 |
| WO | 2013/079174 | 6/2013 |
| WO | 2014/066527 A2 | 5/2014 |

OTHER PUBLICATIONS

Burgess et al. (J. Cell Biol. 111:2129-2138, 1990) (Year: 1990).*
Lazar et al. (Mol. Cell. Biol., 8:1247-1252, 1988) (Year: 1988).*
Brown et al. (J Immunol. May 1996;156(9):3285-91 (Year: 1996).*
Vajdos et al. (J Mol Biol. Jul. 5, 2002;320(2):415-28) (Year: 2002).*
Kermer et al ("Antibody fusion proteins for cancer immunotherapy mimicking iL-15 trans presentation at the 2 tumor site". CIMT Cancer Immunotherapy 8th annual meeting abstractbook 2010 CIMT abstractbook May 26-28, 2010. pp. 1-171. abstract No. 113; p. 163) (Year: 2010).*
Mortier et al (J Biol Chem. Jan. 20, 2006;281(3):1612-9. Epub Nov. 11, 2005) (Year: 2006).*
NCBI database entry for IL-15 accession No. NP_000576.1, downloaded Feb. 7, 2015 from http://www.ncbi.nlm.nih.gov/protein/NP_000576.1 (Year: 2015).*
Kaspar et al (Cancer Res 2007; 67: (10)) (Year: 2007).*
Stone et al., "Design and characterization of a protein superagonist of IL-15 fused with IL-15Rα and a high-affinity T cell receptor", Biotechnol Prog., 28(6), Nov. 2012, pp. 1588-1597.
Notice of Refusal for Japanese Application No. 2016-508046, dated Jan. 23, 2018, 8 pages.
Eisenbeis, C. F., et al. (2004). "Combination immunotherapy of B-cell non-Hodgkin's lymphoma with rituximab and interleukin-2: a preclinical and phase I study." Clin Cancer Res 10(18 Pt 1): 6101-6110.
Konterrnann, R. E. (2012). "Antibody-cytokine fusion proteins." Arch Biochem Biophys 526(2): 194-205.
Pasche, N. and D. Neri (2012). "Immunocytokines: a novel class of potent armed antibodies." Drug Discov Today 17 (11-12): 583-590.
Munger, W., et al. (1995). "Studies evaluating the antitumor activity and toxicity of interleukin-15, a new T cell growth factor: comparison with interleukin-2." Cell Immunol 165(2): 289-293.

Laprevotte, E., et al. (2013). "Recombinant human IL-15 trans-presentation by B leukemic cells from chronic lymphocytic leukemia induces autologous NK cell proliferation leading to improved anti-CD20 immunotherapy." J Immunol 191(7): 3634-3640.
Epardaud, M., et al. (2008). "Interleukin-15/interleukin-15R alpha complexes promote destruction of established tumors by reviving tumor-resident CD8+ T cells." Cancer Res 68(8): 2972-2983.
Gillies, S. D., et al. (1999). "Improving the efficacy of antibody-interleukin 2 fusion proteins by reducing their interaction with Fc receptors." Cancer Res 59(9): 2159-2166.
Gillies, S. D., et al. (2002). "Improved circulating half-life and efficacy of an antibody-interleukin 2 immunocytokine based on reduced intracellular proteolysis." Clin Cancer Res 8(1): 210-216.
Kendra, K., et al. (1999). "Pharmacokinetics and stability of the ch14.18-interleukin-2 fusion protein in mice." Cancer Immunol Immunother 48(5): 219-229.
Halin, C., et al. (2002). "Enhancement of the antitumor activity of interleukin-12 by targeted delivery to neovasculature." Nat Biotechnol 20(3): 264-269.
Gilman, A. L., et al. (2009). "Phase I study of ch14.18 with granulocyte-macrophage colony-stimulating factor and interleukin-2 in children with neuroblastoma after autologous bone marrow transplantation or stem-cell rescue: a report from the Children's Oncology Group." J Clin Oncol 27(1): 85-91.
Cahan, L. D., et al. (1982). "Identification of a human neuroectodermal tumor antigen (OFA-I-2) as ganglioside GD2." Proc Natl Acad Sci U S A 79(24): 7629-7633.
Yuki, N., et al. (1997). "Pathogenesis of the neurotoxicity caused by anti-GD2 antibody therapy." J Neurol Sci 149(2): 127-130.
Svennerholm, L., et al. (1994). "Membrane lipids of adult human brain: lipid composition of frontal and temporal lobe in subjects of age 20 to 100 years." J Neurochem 63(5): 1802-1811.
Birkle, S., et al. (2003). "Role of tumor-associated gangliosides in cancer progression." Biochimie 85(3-4): 455-463.
Mueller, B. M., et al. (1990). "Enhancement of antibody-dependent cytotoxicity with a chimeric anti-GD2 antibody." J Immunol 144(4): 1382-1386.
Imai, M., et al. (2005). "Complement-mediated mechanisms in anti-GD2 monoclonal antibody therapy of murine metastatic cancer." Cancer Res 65(22): 10562-10568.
Cheever, M. A., et al. (2009). "The prioritization of cancer antigens: a national cancer institute pilot project for the acceleration of translational research." Clin Cancer Res 15(17): 5323-5337.
Handgretinger, R., et al. (1995). "A phase I study of human/mouse chimeric antiganglioside GD2 antibody ch14.18 in patients with neuroblastoma." Eur J Cancer 31A(2): 261-267.
Alvarez-Rueda, N., et al. (2007). "Binding activities and antitumor properties of a new mouse/human chimeric antibody specific for GD2 ganglioside antigen." Clin Cancer Res 13(18 Pt 2): 5613s-5620s.
Johannsen, M., et al. (2010). "The tumour-targeting human L19-IL2 immunocytokine: preclinical safety studies, phase I clinical trial in patients with solid tumours and expansion into patients with advanced renal cell carcinoma" Eur J Cancer 46(16): 2926-2935.
Kermer, V., et al. (2014). "Combining antibody-directed presentation of IL-15 and 4-1BBL in a trifunctional fusion protein for cancer immunotherapy." Mol Cancer Ther 13(1): 112-121.
Flies, D. B., et al. (2011). "Blockade of the B7-H1/PD-1 pathway for cancer immunotherapy." Yale J Biol Med 84(4): 409-421.
Nomi, T., et al. (2007). "Clinical significance and therapeutic potential of the programmed death-1 ligand/programmed death-1 pathway in human pancreatic cancer." Clin Cancer Res 13(7): 2151-2157.
Zhou Q. et (2010). "Blockade of programmed death-1 pathway rescues the effector function of tumor-infiltrating T cells and enhances the antitumor efficacy of lentivector immunization." J Immunol 185(9): 5082-5092.
Zitvogel, L. and G. Kroemer (2012). "Targeting PD-1/PD-L1 interactions for cancer immunotherapy." Oncoimmunology 1(8): 1223-1225.
Scott, A.M., et al. (2012)."Antibody therapy of cancer", Nature Reviews Cancer 12: 278-287.

(56) References Cited

OTHER PUBLICATIONS

Allegra, C. J. et al. (2011). "Phase III Trial Assessing Bevacizumab in Stages II and III Carcinoma of the Colon: Results of NSABP Protocol C-08", Journal of Clinical Oncology, 29(1): 11-16.
Office Action for Chinese Patent Application No. 201280037114.2 dated Aug. 19, 2016 (14 pages including English Translation).
Final Notice of Reasons for Rejection for Japanese Patent Application No. 2014-516229 dated Jul. 12, 2016 (9 pages including English Translation).
Singh, H. et al (2007) "Combining adoptive cellular and immunocytokine therapies to Cancer," Ther 8(9): 2736-2745.
R&D Systems, I. (2012) Recombinant Mouse IL-15 Ra Fc Chimera I. R&D Systems, Minneapolis, MN.
Stoklasek, T.A., et al. (2006) "Combined IL-15/IL-15 Ralpha immunotherapy maximizes IL-15 activity in vivo," J Immunol 177(9); 6072-6080.
Vincent, M., et al. (2014) "Highly potent anti-CD20-RLI immunocytokine targeting established human B lymphoa in SCID mouse." MAbs 6(4): 1026-1037.
Singh, H, et al. "Combining Adoptive Cellular and Immunocytokine Therapies to Improve Treatment of B-Lineage Malignanc." Cancer Res 67, No. 6 (Mar. 15, 2007); 2872-80.
International Search Report dated Oct. 2, 2012, in corresponding PCT application PCT/EP2012/002650 (9 pages).
Kermer, V., et al. (2010). Antibody fusion proteins for cancer immunotherapy mimicking IL-15 trans presentation at the tumor site. CIMT Cancer Immunotherapy 8th annual meeting, CIMT abstract book 2010: abstract No. 113, 163.
Ronca, R., et al. (2009). "Delivering cytokines at tumor site: The immunocytokine-conjugated anti-EDB-fibronectin antibody case." Immunobiology 214(9-10): 800-810.
Bessard, A., et al. (2009). "High antitumor activity of RLI, an interleukin-15 (IL-15)-IL-15 receptor alpha fusion protein, in metastatic melanoma and colorectal cancer." Mol Cancer Ther 8(9): 2736-2745.
Bessard, A., et al. (2009). High antitumor activity of RLI, an IL15-IL15Ralpha fusion protein, in metastatic melanoma and colorectal cancer. Tri-Society Annual Conference of the International-Cytokine-Society. Lisbon, Abstract book: Abstract: PP2-064. Abstract.
Singh, H., et al. (2007). "Combining adoptive cellular and immunocytokine therapies to improve treatment of B-lineage malignancy." Cancer Res 67(6): 2872-2880.
Kaspar, M., et al. (2007). "The antibody-mediated targeted delivery of interleukin-15 and GM-CSF to the tumor neovasculature inhibits tumor growth and metastasis." Cancer Res 67(10): 4940-4948.
Wei, X., et al. (2001). "The Sushi domain of soluble IL-15 receptor alpha is essential for binding IL-15 and inhibiting inflammatory and allogenic responses in vitro and in vivo." J Immunol 167(1): 277-282.
Penichet, M. L. and S. L. Morrison (2001). "Antibody-cytokine fusion proteins for the therapy of cancer." J Immunol Methods 248(1-2): 91-101.
Ortiz-Sanchez, E., et al. (2008). "Antibody-cytokine fusion proteins: applications in cancer therapy." Expert Opin Biol Ther 8(5): 609-632.
Aubry, J. (1997). "8B6 Anti-O-Acetyl GD2 Ganglioside." Hybridoma 16(6): 568-568.
Dubois, S., et al. (2008). "Preassociation of IL-15 with IL-15R alpha-IgG1-Fc enhances its activity on proliferation of NK and CD8+/CD44high T cells and its antitumor action." J Immunol 180(4): 2099-2106.
Mortier, E., et al. (2006). "Soluble interleukin-15 receptor alpha (IL-15R alpha)-sushi as a selective and potent agonist of IL-15 action through IL-15R beta/gamma. Hyperagonist IL-15 x IL-15R alpha fusion proteins." J Biol Chem 281(3): 1612-1619.
Vincent, M., et al. (2011). "CS14-6. Development of two IL15 immunocytokines targeting either GD2- or CD20-tumoral bearing cells." Cytokine 56(1): 102.
Kermer, V., et al. (2012). "An antibody fusion protein for cancer immunotherapy mimicking IL-15 trans-presentation at the tumor site." Mol Cancer Ther 11(6): 1279-1288.
Bowie, J. U., et al. (1990). "Deciphering the message in protein sequences: tolerance to amino acid substitutions." Science 247(4948): 1306-1310.
Burgess, W. H., et al. (1990). "Possible dissociation of the heparin-binding and mitogenic activities of heparin-binding (acidic fibroblast) growth factor-1 from its receptor-binding activities by site-directed mutagenesis of a single lysine residue." J Cell Biol 111(5 Pt 1): 2129-2138.
Lazar, E., et al. (1988). "Transforming growth factor alpha: mutation of aspartic acid 47 and leucine 48 results in different biological activities." Mol Cell Biol 8(3): 1247-1252.
Vajdos, F. F., et al. (2002). "Comprehensive functional maps of the antigen-binding site of an anti-ErbB2 antibody obtained with shot-gun scanning mutagenesis." J Mol Biol 320(2): 415-428.
Brown, M., et al. (1996). "Tolerance of single, but not multiple, amino acid replacements in antibody VH CDR 2: a means of minimizing B cell wastage from somatic hypermutation?" J Immunol 156(9): 3285-3291.
NCBI database entry for IL-15 accession No. NP_000576.1, downloaded Mar. 28, 2017 from http://www.ncbi.nlm.nih.gov/protein/NP_000576.1).
Grabstein, K. H., et al. (1994). "Cloning of a T cell growth factor that interacts with the beta chain of the interleukin-2 receptor." Science 264(5161): 965-968.
Hori, T., et al. (1987). "Establishment of an interleukin 2-dependent human T cell line from a patient with T cell chronic lymphocytic leukemia who is not infected with human T cell leukemia/lymphoma virus." Blood 70(4): 1069-1072.
Needleman, S. B. and C. D. Wunsch (1970). "A general method applicable to the search for similarities in the amino acid sequence of two proteins." J Mol Biol 48(3): 443-453.
Pearson, W. R. and D. J. Lipman (1988). "Improved tools for biological sequence comparison." Proc Natl Aced Sci U S A 85(8): 2444-2448.
Edgar, R. C. (2004). "Muscle: multiple sequence alignment with high accuracy and high throughput" Nucleic Acids Res 32(5): 1792-1797.
Zhu, X., et al. (2009). "Novel human interleukin-15 agonists." J Immunol 183(6): 3598-3607.
Riechmann, L., et al. (1988). "Reshaping human antibodies for therapy." Nature 332(6162): 323-327.
Co, M. S., et al. (1991). "Humanized antibodies for antiviral therapy." Proc Natl Aced Sci U S A 88(7): 2869-2873. [cited in the spec. as Queen et al., who is last author].
Tran, M., et al. (2008). "Targeting a tumor-specific laminin domain critical for human carcinogenesis." Cancer Res 68 (8): 2885-2894. [cited in the spec. as Rousselle, who is second author].
Till, M. A., et al. (1989). "Human immunodeficiency virus-infected T cells and monocytes are killed by monoclonal human anti-gp41 antibodies coupled to ricin A chain." Proc Natl Acad Sci U S A 86(6): 1987-1991.
Zago, P., et al. (2009). "Improving human interteron-beta production in mammalian cell lines by insertion of an intronic sequence within its naturally uninterrupted gene." Biotechnol Appl Biochem 52(Pt 3): 191-198.
Campos-da-Paz, M., et al. (2008). "Production of recombinant human factor VIII in different cell lines and the effect of human XBP1 co-expression." Mol Biotechnol 39(2): 155-158.
Cerato E., et al. (1997). "Variable Region Gene Segments of Nine Monoclonal Antibodies Specific to Disialogangliosides (GD2, GD3) and Their O-Acetylated Derivatives." Hybridoma 16(4): 307-316.
Reff, M. E., et al. (1994). "Depletion of B cells in vivo by a chimeric mouse human monoclonal antibody to CD20." Blood 83(2): 435-445.
Lode, H. N., et al. (1997). "Targeted interleukin-2 therapy for spontaneous neuroblastoma metastases to bone marrow." J Natl Cancer Inst 89(21): 1586-1594.
Baker, M. & Carr, F. 2010. Pre-clinical considerations in the assessment of immunogenicity for protein therapeutics. Curr Drug Saf, 5, 308-13.

(56) References Cited

OTHER PUBLICATIONS

Lode, H. N. and R. A. Reisfeld (2000). "Targeted cytokines for cancer immunotherapy." Immunol Res 21(2-3): 279-288.

Huntington, N. D., et al. (2009). "IL-15 trans-presentation promotes human NK cell development and differentiation in vivo." J Exp Med 206(1): 25-34.

Bouchaud, G., et al. (2008). "The exon-3-encoded domain of IL-15Ralpha contributes to IL-15 high-affinity binding and is crucial for the IL-15 antagonistic effect of soluble IL-15Ralpha." J Mol Biol 382(1): 1-12.

Badoual C., et al.(2008). "The soluble alpha chain of interleukin-15 receptor: a proinflammatory molecule associated with tumor progression in head and neck cancer." Cancer Res 68(10): 3907-3914.

Walzer, T., et al. (2007). "Natural killer cell trafficking in vivo requires a dedicated sphingosine 1-phosphate receptor." Nat Immunol 8(12): 1337-1344.

Quemener, A., et al. (2006). "Docking of human interleukin-15 to its specific receptor alpha chain: correlation between molecular modeling and mutagenesis experimental data." Proteins 65(3): 623-636.

Lorenzen, I., et al. (2006). "The structure of the interleukin-15 alpha receptor and its implications for ligand binding." J Biol Chem 281(10): 6642-6647.

Mortier, E., et al. (2004). "Natural, proteolytic release of a soluble form of human IL-15 receptor alpha-chain that behaves as a specific, high affinity IL-15 antagonist." J Immunol 173(3): 1681-1688.

Bernard, J., et al. (2004). "Identification of an interleukin-15alpha receptor-binding site on human interleukin-15." J Biol Chem 279(23): 24313-24322.

Vincent, M., et al. (2013). "Tumor targeting of the IL-15 superagonist RLI by an anti-GD2 antibody strongly enhances its antitumor potency." Int J Cancer 133(3): 757-765.

Gillies, S. D., et al. (2005). "An anti-CD20-IL-2 immunocytokine is highly efficacious in a SCID mouse model of established human B lymphoma." Blood 105(10): 3972-3978.

Xuan, C., et al. (2010). "Targeted delivery of interferon-alpha via fusion to anti-CD20 results in potent antitumor activity against B-cell lymphoma." Blood 115(14): 2864-2871.

Gluck, W. L., et al. (2004). "Phase I studies of interleukin (IL)-2 and rituximab in B-cell non-hodgkin's lymphoma: IL-2 mediated natural killer cell expansion correlations with clinical response." Clin Cancer Res 10(7): 2253-2264.

\* cited by examiner

IL-15 AND IL-15R\ALPHA SUSHI DOMAIN BASED IMMUNOCYTOKINES

The present application is a continuation Patent Application of non-provisional patent application Ser. No. 14/129,188, with a 371(c) date of Jul. 3, 2014, which claims priority to International Application No. PCT/EP2012/002650, filed Jun. 22, 2012, which claims the priority of European Patent Application 11358005.4 filed on Jun. 24, 2011, all of which are incorporated herein by reference in their entireties.

INCORPORATION OF SEQUENCE LISTING

This application contains a sequence listing titled "Sequence Listing.txt," which was created Jul. 19, 2016 and is 68,860 bytes in size. The sequence listing is incorporated herein by reference.

FIELD OF THE INVENTION

The present invention relates to new immunocytokines and to their use as a medicine, in particular for the treatment of cancer.

BACKGROUND

Immunotherapy, in medicine, refers to an array of treatment strategies based on the concept of modulating the immune system to achieve a prophylactic and/or therapeutic goal.

In the past few years, immunotherapy has been used for the treatment or the prevention of several pathologies, particularly cancers. Since the development of the cell fusion technique for the production of monoclonal antibodies, a vast number of monoclonal antibodies have been produced by researchers. Thenafter, other techniques have been developed for the generation of monoclonal antibodies, including the B cell hybridoma technique and the EBV hybridoma technique to produce human monoclonal antibodies.

Monoclonal antibodies (Mab) can be developed to target almost any epitope. The property of specific recognition and binding to particular cells/molecules has encouraged the development of Mabs as diagnostic and therapeutic reagents for a variety of disease states. Recombinant DNA techniques have been used to produce chimeric or humanized antibodies to adapt their administration to humans. Currently, several monoclonal antibodies are commercialized and available for the treatment of cancers, infectious diseases, immune diseases etc. such as RITUXAN®, HERCEPTIN®, AVASTIN®, . . . .

Monoclonal antibodies are targeted molecules and able to localize within a specific zone (cells, tissues . . . ) such as a tumor tissues. This property has also led to the development of Mabs conjugated to various substances (payloads) in an effort to target specific molecules in the tumor sites called tumoral antigens. Such substances (payloads) can be toxins, drugs, radionuclides, prodrug compounds . . . . Many of these linkages involve the chemical conjugation of the reactive moiety (payload) with a given preparation of antibody, a process which can be cumbersome and subject to variation (U.S. Pat. No. 4,671,958).

Among these new molecules, the immunocytokines are of particular interest. Said immunocytokines correspond to fusion proteins comprising an antibody and a cytokine. These proteins retain both antigen-binding capacity and cytokine activity.

The cytokines are a category of signalling proteins and glycoproteins that, like hormones and neurotransmitters, are used extensively in cellular communication. While hormones are secreted by specific organs into the blood, and neurotransmitters are related to neural activity, cytokines are a more diverse class of compounds in terms of origin and purpose. They are produced by a wide variety of hematopoietic and non-hematopoietic cell types and can have effects on both nearby cells or throughout the organism, sometimes strongly depending on the presence of other chemicals. The cytokine family consists mainly of smaller, water-soluble proteins and glycoproteins with a mass of between 8 and 30 kDa. Cytokines are critical to the functioning of both innate and adaptive immune responses. They are often secreted by immune cells which have encountered a pathogen as a way to activate and recruit more immune cells and increase the system's response to the pathogen. However, apart from their role in the development and functioning of the immune system, cytokines are also involved in several developmental processes during embryogenesis.

Among the cytokines, interleukin 15 (IL-15) is a cytokine with structural similarity to IL-2 that is secreted by mononuclear phagocytes (and some other cells) following infection by virus(es) or indirect stimulation by cells recognized as non-self or debilitated. This cytokine induces cell proliferation of natural killer cells; cells of the innate immune system whose main role is to kill virally infected cells. The protein encoded by this gene is a cytokine that regulates T and natural killer cell activation and proliferation.

The construction of immunocytokines on the basis of IL-15 would thus be of particular interest for the combination of the tumor-targeting assets of tumor-specific antibodies with the immunomodulatory effects of interleukin 15. Several immunocytokines using notably interleukin-2 (IL-2) have been already obtained and demonstrated very interesting and encouraging results in phase 2 oncology clinical trials. Some examples of these fusion proteins are described in several patent applications (U.S. Pat. No. 5,645,835, EP 0,305,967, WO 86/01533, EP 0,439,095, and WO 85/00974).

Thus, interleukin 15-based immunocytokine has been produced in HEK-293 cells and is disclosed in International patent application PCT WO 2007/128563 and in KASPAR et al. (*Cancer Research*, vol. 67(10), p: 4940-4948, 2007).

Nevertheless, the inventors established that such interleukin 15-based immunocytokines have a very limited interleukin 15 activity, and that their production is very difficult notably in CHO cells with low yield and many protein contaminants.

Thus, there is still a need for interleukin 15-based immunocytokines that can be used in immunotherapies.

SUMMARY OF THE INVENTION

The invention relates to an immunocytokine comprising:
A) a conjugate, and
B) an antibody or a fragment thereof directly or indirectly linked by covalence to said conjugate,
wherein said conjugate comprises:
(i) a polypeptide comprising the amino acid sequence of interleukin 15 or derivatives thereof, and
(ii) a polypeptide comprising the amino acid sequence of the sushi domain of IL-15Rα or derivatives thereof In a second aspect, the invention relates to a nucleic acid encoding for an immunocytokine as described above.

In a third aspect, the present invention provides a vector comprising a nucleic acid as described above.

In a forth aspect, the present invention relates to a host cell genetically engineered with the polynucleotide or with the vector described previously. The present invention also relates to a method of producing a host cell genetically engineered expressing an immunocytokine according to the invention, said method comprising the steps of: (i) introducing in vitro or ex vivo a nucleic acid or a vector as described above into a host cell, (ii) culturing in vitro or ex vivo the recombinant host cell genetically engineered obtained and (iii), optionally, selecting the cells which express and/or secrete said immunocytokine.

In a preferred embodiment said host cell genetically engineered is an animal cell, and preferably a CHO cell.

In a fifth aspect, the present invention provides a pharmaceutical composition comprising the immunocytokine as described above, a nucleic acid encoding thereof, or a nucleic acid vector comprising said nucleic acid, eventually associated with a pharmaceutically acceptable carrier.

In a preferred embodiment, said composition comprises a further therapeutic agent, which is preferably an anticancer agent.

In a sixth aspect, the present invention relates to a pharmaceutical composition as described previously for treating cancer in a subject.

In seventh aspect, the present invention relates to the products containing:

(i) an immunocytokine as describe above, a nucleic acid sequence coding therefore, or a vector comprising such a nucleic acid sequence, and (ii) a therapeutic agent, preferably an anticancer agent, as a combined preparation for simultaneous, separate, or sequential use for treating cancer in a subject.

In an eighth aspect, the present invention relates to a method for treating cancer in a subject comprising the step of administrating to said subject a pharmaceutical composition as described previously.

In a final aspect, the present invention relates to a method for treating cancer comprising the step of simultaneously, separately, or sequentially administrating to a subject in need thereof a therapeutically effective amount of:

(i) an immunocytokine as describe above, a nucleic acid sequence coding therefore, or a vector comprising such a nucleic acid sequence, and (ii) a therapeutic agent, preferably an anticancer agent.

DETAILED DESCRIPTION

Figure 1:
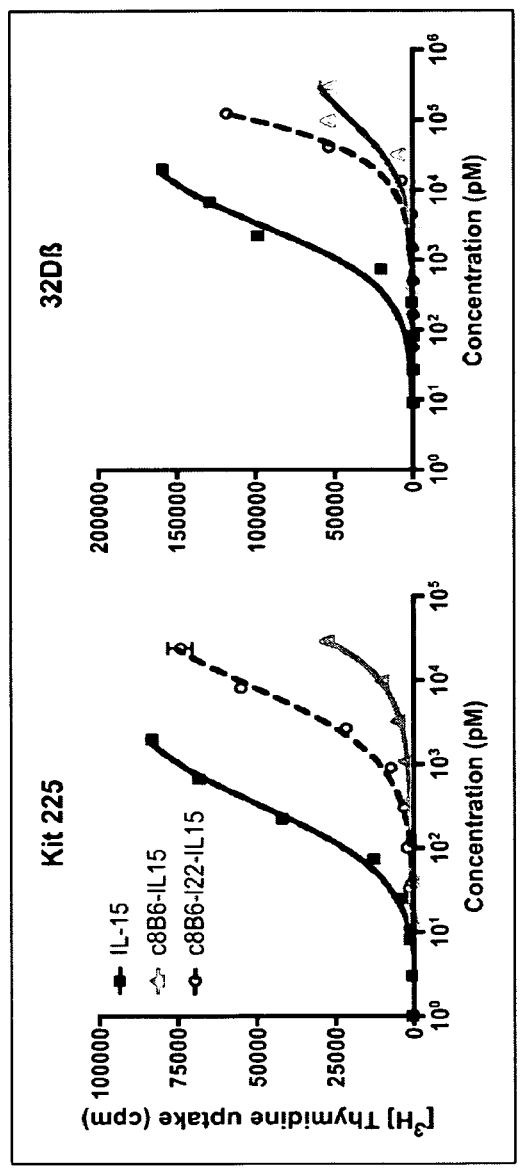
FIG. 1 shows the activity of IL15 anti-CD20 immunocytokines as compared to IL15.

The present invention is based on the discovery by the present inventors that, whereas the production of an immunocytokine comprising interleukin 15 leads to the loss of more than 90% of interleukin 15 activity, the production of RLI-based immunocytokines leads to innovative IL15 immunocytokines presenting a powerful biological activity on αβγ and βγ immune cells that is largely superior to IL-15-based immunocytokines.

Surprisingly, RLI-based immunocytokines with a full IgG monoclonal antibody present improved biological efficacy on βγ immune cells as compared to RLI alone or to scFv fragment antibody. This surprising gain of activity on βγ immune cells could be critical in terms of activation/reactivation of NK cells and T lymphocytes in the immunosuppressive environment.

Still surprisingly, and whereas an interleukin 15 immunocytokine necessitates the presence of a linker between the immunoglobulin and the interleukin 15 moieties so as to be active; the immunocytokine of the invention present a similar interleukin 15 activity with or without any linker between its respective immunoglobulin and cytokine parts. This unnecessary presence of a linker region could represent powerful arguments in terms of fusion protein immunogenicity, limiting the hinge regions generating novel antigenic epitope and immunogenicity and in terms of production yield with limited cleaved forms.

Still surprisingly, the immunocytokines of the invention are IL-15 superagonist showing an increased activity (—i.e. 10 to 100 fold) as compared to RLI alone.

Moreover, the inventors obtained a good yield of production of the immunocytokine of the invention in CHO cells, and this with a yield of more than 90%. This is surprising since the production in the same cells of interleukin 15 immunocytokine in CHO cells was very difficult.

As immunocytokines have a limited serum half-life traditionally and as immunocytokines-related tumor localization rate is a critical issue to generate a robust antitumor effect, the specific biological activity of RLI-based immunocytokines permitting to activate immune cells at very low concentration represent an important innovative step in this field and could improve the efficacy of such biological compounds in cancer patients.

Finally, the strong activity of the immunocytokine of the invention enables to forecast a realistic therapeutic use for this immunocytokine, which should be administrated by injection at a dose of 2.5-1 mg/kg of subject or less, and even at a dose of 0.1 mg/kg or less. In fact, the low activity of interleukin 15 immunocytokines such as the one disclosed in International patent application WO 2007/128563 does not enable any realistic therapeutic use (i.e. obtaining a therapeutic effect required a dose of more than 20 µg immunocytokine with four daily injections in a mouse tumor model suggesting the need of a dose of more than 5 mg/kg immunocytokine for obtaining some therapeutic effect).

Consequently, one aspect the present invention relates to an immunocytokine comprising of:

A) a conjugate, and

B) an antibody or a fragment thereof directly or indirectly linked by covalence to said conjugate, wherein said conjugate comprises:

(i) a polypeptide comprising the amino acid sequence of interleukin 15 or derivatives thereof, and (ii) a polypeptide comprising the amino acid sequence of the sushi domain of IL-15Rα or derivatives thereof.

The term "immunocytokine" refers to a molecule comprising an antibody or fragments thereof directly or indirectly linked by covalence to a cytokine or derivates thereof. Said antibody and said cytokine can be linked by a linker peptide.

Conjugate of the Immunocytokine of the Invention

The term "interleukin 15" in its general meaning in the art and refers to a cytokine with structural similarity to IL-2 (GRABSTEIN et al., *Science*, vol. 264(5161), p: 965-968, 1994). This cytokine is also known as IL-15, IL15 or MGC9721. This cytokine and IL-2 share many biological activities and they were found to bind common hematopoietic receptor subunits. Thus, they may compete for the same receptor, negatively regulating each other's activity. It has been established that IL-15 regulates T and natural killer cells activation and proliferation, and that the number of CD8+ memory cells is shown to be controlled by a balance between this cytokine and IL2. IL-15 activity can be measured by determining its proliferation induction on kit225 cell line (HORI et al., *Blood*, vol. 70(4), p: 1069-72, 1987), as disclosed in the Examples.

Said IL-15 or derivatives thereof have at least 10% of the activity of human interleukin-15 on the proliferation induction of kit225 cell line, preferably at least 25% and more preferably at least 50%.

Said interleukin 15 is a mammalian interleukin 15, preferably a primate interleukin 15, and more preferably a human interleukin 15.

Mammalian interleukin 15 can be simply identified by the skilled person. As an example, one can cite Interleukin 15 from *Sus scrofa* (Accession number ABF82250), from *Rattus norvegicus* (Accession number NP_037261), from *Mus musculus* (Accession number NP_032383), from *Bos taurus* (Accession number NP_776515), from *Oryctolagus cuniculus* (Accession number NP_001075685), from *Ovies aries* (Accession number NP_001009734), from *Felis catus* (Accession number NP_001009207), from *Macaca fascicularis* (Accession number BAA19149), from *Homo sapiens* (Accession number NP_000576), from *Macaca mulatta* (Accession number NP_001038196), from *Cavia porcellus* (Accession number NP_001166300), or from *Chlorocebus sabaeus* (Accession number ACI289).

As used herein, the term "mammalian interleukin 15" refers to the consensus sequence SEQ ID NO: 1.

Primate interleukin 15 can be simply identified by the skilled person. As an example, one can cite Interleukin 15 from *Sus scrofa* (Accession number ABF82250), from *Oryctolagus cuniculus* (Accession number NP_001075685), from *Macaca fascicularis* (Accession number BAA19149), from *Homo sapiens* (Accession number NP_000576), from *Macaca mulatta* (Accession number NP_001038196), or from *Chlorocebus sabaeus* (Accession number ACI289).

As used herein, the term "primate interleukin 15" refers to the consensus sequence SEQ ID NO:2.

Human interleukin 15 can be simply identify by the skilled person and refers to the amino acids sequence SEQ ID NO:3.

As used herein, the term "interleukin 15 derivatives" refers to an amino acid sequence having a percentage of identity of at least 92.5% (i.e. corresponding to about 10 amino acids substitutions) with an amino acid sequence selected in the group consisting of SEQ ID NO:1, SEQ ID NO:2 and SEQ ID NO:3, preferably of at least 96% (i.e. corresponding to about 5 amino acids substitutions), and more preferably of at least 98.5% (i.e. corresponding to about 2 amino acids substitutions) or of at least 99% i.e. corresponding to about 1 amino acid substitution). Such derivatives can be simply identified by the skilled person in view of its personal knowledge and of the teaching of the present patent application. As an example of such derivatives, one can cite those described in the International Patent Application PCT WO 2009/135031. It will also be understood that natural amino acids may be replaced by chemically modified amino acids. Typically, such chemically modified amino acids increase the polypeptide half life.

As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compare the local regions of similarity. The best sequences alignment to perform comparison can be realized, beside by a manual way, by using the global homology algorithm developed by SMITH and WATERMAN (*Ad. App. Math.*, vol. 2, p: 482, 1981), by using the local homology algorithm developed by NEDDLEMAN and WUNSCH (*J. Mol. Biol.*, vol. 48, p: 443, 1970), by using the method of similarities developed by PEARSON and LIPMAN (*Proc. Natl. Acad. Sci. USA*, vol. 85, p: 2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C., *Nucleic Acids Research*, vol. 32, p: 1792, 2004). To get the best local alignment, one can preferably use the BLAST software with the BLOSUM 62 matrix. The identity percentage between two sequences of amino acids is determined by comparing these two sequences optimally aligned, the amino acids sequences being able to encompass additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

Preferably, the interleukin 15 derivatives are IL-15 agonist or superagonist. One skilled in the art can simply identified an IL-15-agonist or -superagonist. As a example of IL-15-agonist or -superagonist, one can cite the ones disclosed in the International patent application WO 2005/085282 or in ZHU et al. (*J. Immunol.*, vol. 183(6), p: 3598-607, 2009).

Still preferably, said IL-15 agonist or superagonist is selected in the group comprising/consisting of L45D, L45E, S51D, L52D, N72D, N72E, N72A, N72S, N72Y and N72P (in reference to sequence of human IL-15, SEQ ID NO:3).

As used herein the term "the sushi domain of IL-15Rα" has its general meaning in the art and refers to a domain beginning at the first cysteine residue (C1) after the signal peptide of IL-15Rα, and ending at the fourth cysteine residue (C4) after said signal peptide. Said sushi domain corresponding to a portion of the extracellular region of IL-15Rα is necessary for its binding to IL-15 (WEI et al., *J. Immunol.*, vol. 167(1), p: 277-282, 2001).

Said sushi domain of IL-15Rα or derivatives thereof has at least 10% of the binding activity of the sushi domain of human IL-15Rα to human interleukin-15, preferably at least 25% and more preferably at least 50%. Said binding activity can be simply determined by the method disclosed in WEI et al. (abovementioned, 2001).

Said sushi domain of the IL-15Rα is the sushi domain of a mammalian IL-15Rα, preferably the sushi domain of a primate IL-15Rα and more preferably the sushi domain of the human IL-15Rα.

The sushi domain of a mammalian IL-15Rα can be simply identified by the skilled person. As an example, one can cite the sushi domain of a IL-15Rα from *Rattus norvegicus* (Accession number XP_002728555), from *Mus musculus* (Accession number EDL08026), from *Bos taurus* (Accession number XP_002692113), from *Oryctolagus cuniculus* (Accession number XP_002723298), from *Macaca fascicularis* (Accession number ACI42785), from *Macaca nemestrina* (Accession number ACI42783), from *Homo sapiens* (Accession number CAI41081), from *Macaca mulatta* (Accession number NP_001166315), *Pongo abelii* (Accession number XP_002820541), *Cercocebus torquatus* (Accession number ACI42784), *Callithrix jacchus* (Accession number XP_002750073), or from *Cavia porcellus* (Accession number NP_001166314).

As used herein, the term "sushi domain of a mammalian IL-15Rα" refers to the consensus sequence SEQ ID NO:4.

Preferably, the polypeptide comprising the amino acid sequence of the sushi domain of a mammalian IL-15Rα refers to the consensus sequence SEQ ID NO:5.

The sushi domain of a primate IL-15Rα can be simply identified by the skilled person. As an example, one can cite sushi domains of IL-15Rα from *Oryctolagus cuniculus*, from *Macaca fascicularis*, from *Macaca nemestrina*, from *Homo sapiens*, from *Macaca mulatta*, *Pongo abelii*, *Cercocebus torquatus*, or *Callithrix jacchus*.

As used herein, the term "sushi domain of a primate IL-15Rα" refers to the consensus sequence SEQ ID NO:6.

Preferably, the polypeptide comprising the amino acid sequence of the sushi domain of a primate IL-15Rα refers to the consensus sequence SEQ ID NO:7.

The sushi domain of human IL-15Rα can be simply identified by the skilled person and refers to the amino acids sequence SEQ ID NO:8.

Preferably, the polypeptide comprising the amino acid sequence of the sushi domain of human IL-15Rα refers to SEQ ID NO:9.

As used herein, the term "derivatives of the sushi domain of the IL-15Rα" refers to an amino acid sequence having a percentage of identity of at least 92% (i.e. corresponding to about 5 amino acids substitutions) with an amino acid sequence selected in the group consisting of SEQ ID NO:4, SEQ ID NO:5, SEQ ID NO:6, SEQ ID NO:7, SEQ ID NO:8, and SEQ ID NO:9, preferably of at least 96% (i.e. corresponding to about 2 amino acids substitutions), and more preferably of at least 98% (i.e. corresponding to about 1 amino acids substitutions). Such derivatives comprise the four cysteine residues of the sushi domain of L-15Rα and can be simply identified by the skilled person in view of his/her general knowledge and of the teaching of the present patent application. It will also be understood that natural amino acids may be replaced by chemically modified amino acids. Typically, such chemically modified amino acids enable to increase the polypeptide half life.

According to a preferred embodiment, the conjugate comprises (ii) a polypeptide comprising the amino acid sequence of the sushi and hinge domains of IL-15Rα or derivatives thereof.

The IL-15Rα hinge domain is defined as the amino acid sequence that begins at the first amino residue after the sushi domain and that ends at the last amino acid residue before the first potential site of glycosylation. In human IL-15Rα, the amino acid sequence of the hinge region consists of the fourteen amino acids which are located after the sushi domain of this IL-15Ralpha, in a C-terminal position relative to said sushi domain, i.e., said IL-15Ralpha hinge region begins at the first amino acid after said (C4) cysteine residue, and ends at the fourteenth amino acid (counting in the standard "from N-terminal to C-terminal" orientation).

Said sushi and hinge domains of IL-15Rα are the sushi and hinge domains of a mammalian IL-15Rα, preferably the sushi and hinge domains of a primate IL-15Rα and more preferably the sushi and hinge domains of the human IL-15Rα.

The amino acid sequence of the sushi and hinge domains of a mammalian IL-15Rα can be simply identified by the skilled person. As used herein, the term "sushi and hinge domains of a mammalian IL-15Rα" refers to the consensus sequence SEQ ID NO:10.

The amino acid sequence of the sushi and hinge domains of a primate IL-15Rα can be simply identified by the skilled person. As used herein, the term "sushi and hinge domains of a primate IL-15Rα" refers to the consensus sequence SEQ ID NO: 11.

The amino acid sequence of the sushi and hinge domains of human IL-15Rα can be simply identified by the skilled person. As used herein, the term "sushi and hinge domains of human IL-15Rα" refers to the consensus sequence SEQ ID NO:12.

As used herein, the term "derivatives of the sushi and hinge domains of IL-15Rα" refers to an amino acid sequence having a percentage of identity of at least 93% (i.e. corresponding to about 5 amino acids substitutions) with an amino acid sequence selected in the group consisting of SEQ ID NO: 10, SEQ ID NO: 11, and SEQ ID NO: 12, preferably of at least 97% (i.e. corresponding to about 2 amino acids substitutions), and more preferably of at least 98% (i.e. corresponding to about 1 amino acids substitution). Such derivatives comprise the four cysteine residues of the sushi domain of L-15Rα and can be simply identified by the skilled person in view of its general knowledge and of the teaching of the present patent application. It will also be understood that natural amino acids may be replaced by chemically modified amino acids. Typically, such chemically modified amino acids enable to increase the polypeptide half life.

Both polypeptides i) and ii) of the conjugate may be linked non-covalently such as in the complex disclosed in U.S. Pat. No. 8,124,084 B2. Said conjugate or complex can be simply obtained by providing a suitable amount of the polypeptide i), providing a suitable amount of the polypeptide ii), admixing both polypeptides under suitable pH and ionic conditions for a duration sufficient to allow complex (i.e. conjugate) formation, and optionally concentrating or purifying said complex. The polypeptides of the complex (i.e. conjugate) can be formed, for example, using a peptide synthesizer according to standard methods; by expressing each polypeptide separately in a cell or cell extract, then isolating and purifying the polypeptide. Optionally, the therapeutic polypeptide complex of the invention can be formed by expressing both polypeptides i) and ii) in the same cell or cell extract, then isolating and purifying the complexes, for example, using chromatographic techniques, such as affinity chromatography with antibodies to the lymphokine portion, the lymphokine receptor portion, or to the complex.

Both polypeptides i) and ii) of the conjugate may be also covalently linked using bifunctional protein coupling agents or in a fusion protein.

Bifunctional protein coupling agents are well known from the skilled person such as methods using them, and include, as examples, N-succinimidyl (2-pyridyldithio) propionate (SPDP), succinimidyl (N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

The term "fusion protein" refers to a protein created through the joining of two or more genes which originally coded for separate proteins. It is also known as a chimeric protein. Translation of this fusion gene results in a single polypeptide with functional properties deriving from each of the original proteins. Recombinant fusion proteins are created artificially by recombinant DNA technology for use in biological research or therapeutics. A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

In a preferred embodiment, the conjugate is a fusion protein.

The amino acid sequence of interleukin 15 or derivatives thereof can be in a C-terminal or in an N-terminal position relative to the amino acid sequence of the sushi domain of IL-15Rα or derivatives thereof. Preferably, the amino acid sequence of the interleukin 15 or derivatives thereof is in a C-terminal position relative to the amino acid sequence of the sushi domain of IL-15Rα or derivatives thereof.

The amino acid sequence of interleukin 15 or derivatives thereof and the amino acid sequence of the sushi domain of IL-15Rα or derivatives thereof may be separated by a first "linker" amino acid sequence. Said first "linker" amino acid sequence may be of a length sufficient to ensure that the fusion protein form proper secondary and tertiary structures.

The length of the first linker amino acid sequence may vary without significantly affecting the biological activity of the fusion protein. Typically, the first linker amino acid sequence comprises at least one, but less than 30 amino acids e.g., a linker of 2-30 amino acids, preferably of 10-30 amino acids, more preferably of 15-30 amino acids, still more preferably of 15-25 amino acids, most preferably of 18-22 amino acids.

Preferred linker amino acid sequences are those which allow the conjugate to adopt a proper conformation (i.e., a conformation allowing a proper signal transducing activity through the IL-15Rbeta/gamma signaling pathway).

The most suitable first linker amino acid sequences (1) will adopt a flexible extended conformation, (2) will not exhibit a propensity for developing ordered secondary structure which could interact with the functional domains of fusion proteins, and (3) will have minimal hydrophobic or charged character which could promote interaction with the functional protein domains.

Preferably, the first linker amino acid sequence comprises near neutral amino acids selected in the group comprising Gly (G), Asn (N), Ser (S), Thr (T), Ala (A), Leu (L), and Gln (Q), most preferably in the group comprising Gly (G), Asn (N), and Ser (S).

Examples of linker sequences are described in U.S. Pat. Nos. 5,073,627 and 5,108,910.

Illustrative flexible linkers that are more particularly suitable for the present invention include those coded by the sequences of SEQ ID NO: 13 (SGGSGGGGSGGGSGGGGSLQ), SEQ ID NO:14 (SGGSGGGGSGGGSGGGGSGG) or SEQ ID NO: 15 (SGGGSGGGGSGGGGSGGGSLQ).

Antibody of the Immunocytokine of the Invention

The term "antibody" refers to an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively. Each heavy chain is comprised of a N-term heavy chain variable region (abbreviated herein as HCVR) and a heavy chain constant region. The heavy chain constant region is comprised of three domains (CH1, CH2, and CH3) for IgG, IgD, and IgA; and 4 domains (CH1, CH2, CH3, andCH4) for IgM and IgE. Each light chain is comprised of a N-term light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions. The functional ability of the antibody to bind a particular antigen depends on the variable regions of each light/heavy chain pair, and is largely determined by the CDRs.

The term "antibody", as used herein, refers to a monoclonal antibody per se. A monoclonal antibody can be a human antibody, chimeric antibody and/or humanized antibody.

Advantageously, the term antibody refers to an IgG, such as IgG1, IgG2 (IgG2a or IgG2b), IgG3 and IgG4. Preferably, the term antibody refers to IgG1 or IgG2, and more preferably to IgG2a.

"Chimeric antibody" means an antibody that is composed of variables regions from a murine immunoglobulin and of constant regions of a human immunoglobulin. This alteration consists simply of substituting the constant region of a human antibody with the murine constant region, thus resulting in a human/murine chimera which may have sufficiently low immunogenicity to be acceptable for pharmaceutical use. A number of methods for producing such chimeric antibodies have yet been reported, thus forming part of the general knowledge of the skilled artisan (See, e.g., U.S. Pat. No. 5,225,539).

"Humanized antibody" means an antibody that is composed partially or fully of amino acid sequences derived from a human antibody germline by altering the sequence of an antibody having non-human complementarity determining regions (CDR). This humanization of the variable region of the antibody and eventually the CDR is made by techniques that are by now well known in the art. As an example, British Patent Application GB 2188638A and U.S. Pat. No. 5,585,089 disclose processes wherein recombinant antibodies are produced where the only portion of the antibody that is substituted is the complementarity determining region, or "CDR". The CDR grafting technique has been used to generate antibodies which consist of murine CDRs, and human variable region framework and constant regions (See. e. g., RIECHMANN et al., Nature, vol. 332, p: 323-327, 1988). These antibodies retain the human constant regions that are necessary for Fc dependent effector function, but are much less likely to evoke an immune response against the antibody. As an example, the framework regions of the variable regions are substituted by the corresponding human framework regions leaving the non-human CDR substantially intact, or even replacing the CDR with sequences derived from a human genome (See e.g. Patent application US 2006/25885). Fully human antibodies are produced in genetically modified mice whose immune systems have been altered to correspond to human immune systems. As mentioned above, it is sufficient for use in the methods of the invention, to employ an immunologically specific fragment of the antibody, including fragments representing single chain forms.

A humanized antibody again refers to an antibody comprising a human framework, at least one CDR from a non-human antibody, and in which any constant region present is substantially identical to a human immunoglobulin constant region, i. e., at least about 85 or 90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody. As an example, the design of humanized immunoglobulins may be carried out as follows: when an amino acid falls under the following category, the framework amino acid of a human immunoglobulin to be used (acceptor immunoglobulin) is replaced by a framework amino acid from a CDR-providing non-human immunoglobulin (donor immunoglobulin): (a) the amino acid in the human framework region of the acceptor immunoglobulin is unusual for human immunoglobulin at that position, whereas the corresponding amino acid in the donor immunoglobulin is typical for human immunoglobulin at that position; (b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model (QUEEN et al., Proc. Natl. Acad. Sci. USA, vol. 88, p: 2869, 1991). When each of the amino acids in the human framework region of the acceptor immunoglobulin and a corresponding amino acid in the donor immunoglobulin is unusual for human immunoglobulin at that position, such an amino acid is replaced by an amino acid typical for human immunoglobulin at that position.

The term "antibody fragment" as used herein refers to antibody fragment capable of reacting with the same antigen than its antibody counterpart. Such fragments can be simply identified by the skilled person and comprise, as an example, $F_{ab}$ fragment (e.g., by papain digestion), $F_{ab}'$ fragment (e.g., by pepsin digestion and partial reduction), $F(_{ab}')_2$ fragment (e.g., by pepsin digestion), $F_{acb}$ (e.g., by plasmin digestion), $F_d$ (e.g., by pepsin digestion, partial reduction and reaggregation), and also $scF_v$ (single chain Fv; e.g., by molecular biology techniques) fragment are encompassed by the invention.

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(_{ab}')_2$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

Preferably, said antibody fragment is a scFv fragment.

In a preferred embodiment, said antibody or fragment thereof is directed against an antigen related to tumor neovascularization or to tumor extracellular matrix, or against a tumoral antigen.

As used herein, an "antigen related to tumor neovascularization" refers to an antigen which is expressed by the neo-synthetized blood vessels present in the tumor.

As an example of such antigen, one can cite the EDA and the EDB domains of fibronectin, Endosalin/TEM1, Endoglin/105, PSMA or B7-H4.

As used herein, As used herein, a "antigen related to tumor extracellular matrix" refers to an antigen which is expressed in the extracellular matrix present in the tumor.

As an example of such antigen, one can cite the G45 fragment of laminin-332 (ROUSSELLE et al., Cancer Research, vol. 68(8), p: 2885-94, 2008).

As used herein a "tumoral antigen" refers to an antigenic substance produced in tumor cells. Many tumoral antigen are well known from the skilled person and one can cite, as non limiting examples, CD-20, CEA, EGFR, GD2, EPCAM, MUC1, PSMA, CD-19, GD3, GM1, CAIX, GD2-O-acetylated or HER2.

CD-20 is a non-glycosylated phosphoprotein expressed during early pre-B cell development and remains until plasma cell differentiation. Specifically, the CD20 molecule may regulate a step in the activation process which is required for cell cycle initiation and differentiation and is usually expressed at very high levels on neoplastic ("tumor") B cells. CD20, by definition, is present on both "normal" B cells as well as "malignant" B cells. Thus, the CD20 surface antigen has the potential of serving as a candidate for "targeting" of B cell lymphomas.

Concerning the antibodies directed against CD-20, one can cite rituximab ("RITUXAN®") (U.S. Pat. No. 5,736, 137); the yttrium-[90]-labeled 2B8 murine antibody designated "Y2B8" or "Ibritumomab Tiuxetan" ZEVALIN® (U.S. Pat. No. 5,736,137); murine IgG2a "BI," also called "Tositumomab," optionally labeled with $^{131}$I to generate the "$^{131}$I-BI" antibody (iodine 131 tositumomab, BEXXAR®) (U.S. Pat. No. 5,595,721); and humanized 2H7; Ofatumumab, a fully humanized IgG1 against a novel epitope on CD20 huMax-CD20 (International patent application PCT WO 2004/035607). Among them, rituximab, ibritumomab tiuxetan, and tositumomab received market approval for the treatment of specific lymphoma, and Ofatumumab received market approval for the treatment of specific leukemia.

The CEA (carcinoembryonic antigen) glycoprotein is a tumor marker involved in cell adhesion.

Concerning the antibodies directed against CEA, one can cite arcitumomab (IMMUNOMEDICS).

The ErbB receptors are expressed in various tissues of epithelial, mesenchymal and neuronal origin. Under normal conditions, activation of the ErbB receptors is controlled by the spatial and temporal expression of their ligands, which are members of the EGF family of growth factors. Ligand binding to ErbB receptors induces the formation of receptor homo- and heterodimers and activation of the intrinsic kinase domain, resulting in phosphorylation on specific tyrosine kinase residues within the cytoplasmic tail. These phosphorylated residues serve as docking sites for various proteins, the recruitment of which leads to the activation of intracellular signaling pathways. Among ErbB receptors, EGFR and HER2 are known to play an essential role in regulating cell proliferation and differentiation. They have a strong tendency to assemble with other HER receptors into homo- and/or heterodimers upon extracellular growth factor binding, which results in various forms of signal transduction pathways activation, leading to either apoptosis, survival, or cell proliferation.

Concerning the antibodies directed against EGFR, one can cite the humanized monoclonal antibody 425, also designated as matuzumab (hMAb 425, U.S. Pat. No. 5,558, 864; EP 0531 472), the chimeric monoclonal antibody 225 (cMAb 225), also designated as cetuximab (ERBITUX®; U.S. Pat. No. 7,060,808), and the fully human anti-EGFR antibody panitumumab (VECTIBIX®; U.S. Pat. No. 6,235, 883). Among them, cetuximab and panitumumab were demonstrated to inhibit human colorectal tumors in vivo and both received marked approval.

Concerning the antibodies directed against Her2, one can cite the recombinant humanized version of the mouse antibody 4D5 (U.S. Pat. No. 5,677,171), designated as huMAb4D5-8, rhuMAb HER2, trastuzumab, or HERCEPTIN® (U.S. Pat. No. 5,821,337). This antibody received marketing approval in 1998 for the treatment of patients with metastatic breast cancer whose tumors overexpress the ErbB2 protein.

GD2 is a disialoganglioside expressed on tumors of neuroectoderma origin, including neuroblastoma and melanoma.

Concerning the antibodies directed against GD2, one can cite the murine IgG3 monoclonal antibody 3F8, which has been used in the treatment of neuroblastoma, or the murine IgG3 monoclonal antibody 8B6, which is specific of the O-acetylated form of GD2 (International patent application PCT WO 2008/043777).

Preferably, the antibody is directed against CD-20 (e.g. rituximab disclosed in U.S. Pat. No. 5,736,137), GD2-O-acetylated (e.g. the one disclosed in International patent application PCT WO 2008/043777) or HER2 (e.g. trastuzumab or HERCEPTIN® disclosed in U.S. Pat. No. 5,821, 337).

Both conjugate and antibody or fragment thereof may be covalently linked using bifunctional protein coupling agents or in a fusion protein.

Bifunctional protein coupling agents methods are well known by the skilled person and have been previously disclosed. As an example, the skilled person can use the method disclosed in TILL et al. (*Proc. Natl. Acad. U.S.A.*, vol. 86(6), p: 1987-91, 1989)

In a preferred embodiment, the immunocytokine is a fusion protein.

In another preferred embodiment, the immunocytokine is a complex, preferably a complex comprising a conjugate between the polypeptides i) and ii), wherein the polypeptide i) or ii) is fused to an antibody or fragment thereof.

The polypeptide i), the polypeptide ii), or the conjugate can be in a C-terminal or in an N-terminal position relative to the amino acid sequence of the antibody or fragment thereof.

Preferably, the conjugate is a fusion protein and the amino acid sequence of the conjugate is in a C-terminal position relative to the amino acid sequence of the antibody or fragment thereof, most preferably in a C-terminal position relative to the amino acid sequence of at least one of the heavy chain constant region of the antibody or fragment thereof.

The amino acid sequence of the conjugate and the amino acid sequence of the antibody or fragment thereof may be separated or not by a second "linker" amino acid sequence.

In a particular embodiment, the immunocytokine of the invention is a fusion protein wherein the conjugate and the antibody or fragment thereof are not separated by any linker.

In fact, the inventors have surprisingly established that the immunocytokine of the invention does not necessitate any linker between the immunoglobulin and cytokine parts so as to be active.

As for the first linker amino acid sequence, said second "linker" amino acid sequence may be of a length sufficient to ensure that the fusion protein form proper secondary and tertiary structures.

The length of the first linker amino acid sequence may vary without significantly affecting the biological activity of the fusion protein. Typically, the first linker amino acid sequence comprises at least one, but less than 30 amino acids e.g., a linker of 2-30 amino acids, preferably of 10-30 amino acids, more preferably of 15-30 amino acids, most preferably of 15-25 amino acids.

As for the first linker amino acid sequence, the most suitable second linker amino acid sequences (1) will adopt a flexible extended conformation, (2) will not exhibit a propensity for developing ordered secondary structure which could interact with the functional domains of fusion proteins, and (3) will have minimal hydrophobic or charged characteristics which could promote interaction with the functional protein domains.

Preferably, the second linker amino acid sequence comprises near neutral amino acid selected in the group comprising Gly (G), Asn (N), Ser (S), Thr (T), Ala (A), Leu (L), and Gln (Q), most preferably in the group comprising Gly (G), Asn (N), and Ser (S).

As an example of a second linker amino acid sequence which is suitable for the present invention, one can cite the sequence SEQ ID NO:16 (SGGGGSGGGGSGGGGSGGGGSG) or SEQ ID NO:17 (AAGGGSGGGSGGGGSGGGGSAA).

Nucleic Acids, Vectors and Recombinant Host Cells

In a second aspect the present invention relates to a nucleic acid encoding for a immunocytokine as described above, preferably an immunocytokine corresponding to a fusion protein.

Said nucleic acid corresponds to RNA or DNA, preferably to DNA.

According to a preferred embodiment, the nucleic acid encoding the immunocytokine of the invention is operatively linked to a gene expression sequence, which directs the expression of the nucleic acid within a prokarotic or an eukaryotic cell, preferably within an eukaryotic cell. The "gene expression sequence" is any regulatory nucleotide sequence, such as a promoter sequence or promoter-enhancer combination, which facilitates the efficient transcription and translation of the immunocytokine nucleic acid to which it is operatively linked. The gene expression sequence may, for example, be a mammalian or viral promoter, such as a constitutive or inducible promoter.

Constitutive mammalian promoters include, but are not limited to, the promoters for the following genes: hypoxanthine phosphoribosyl transferase (HPTR), adenosine deaminase, pyruvate kinase, beta.-actin promoter, muscle creatine kinase promoter, human elongation factor promoter and other constitutive promoters. Exemplary viral promoters which function constitutively in eukaryotic cells include, for example, promoters from the simian virus (e.g., SV40), papilloma virus, adenovirus, human immunodeficiency virus (HIV), cytomegalovirus (CMV), Rous sarcoma virus (RSV), hepatitis B virus (HBV), the long terminal repeats (LTR) of Moloney leukemia virus and other retroviruses, and the thymidine kinase promoter of herpes simplex virus. Other constitutive promoters are known to those of ordinary skill in the art.

The promoters useful as gene expression sequences of the invention also include inducible promoters. Inducible promoters are expressed in the presence of an inducing agent. For example, the metallothione in promoter is induced to promote transcription and translation in the presence of certain metal ions. Others inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operationally joined nucleic acid. The gene expression sequences optionally include enhancer sequences or upstream activator sequences as desired. As used herein, the nucleic acid sequence encoding the immunocytokine of the invention and the gene expression sequence are said to be "operationally linked" when they are covalently linked in such a way as to place the expression or transcription and/or translation of the immunocytokine of the invention coding sequence under the influence or control of the gene expression sequence.

Two DNA sequences are said to be operationally linked if induction of a promoter in the 5' gene expression sequence results in the transcription of the immunocytokine of the invention and if the nature of the linkage between the two DNA sequences does not (1) result in the introduction of a frame-shift mutation, (2) interfere with the ability of the promoter region to direct the transcription of the immunocytokine of the invention, or (3) interfere with the ability of the corresponding RNA transcript to be translated into a protein. Thus, a gene expression sequence would be operationally linked to a nucleic acid sequence coding for the immunocytokine of the invention if the gene expression sequence were capable of effecting transcription of that nucleic acid sequence such that the resulting transcript is translated into the desired polypeptide.

Advantageously, said nucleic acid sequence comprises an intron, since pre-mRNA molecules has often been demonstrated to improve production yields of recombinant molecules. Any sequences of intron may be sued, and as an example, one can cite tone ones disclosed in ZAGO et al. (*Biotechnol. Appl. Biochem.*, vol. 52(Pt 3), p: 191-8, 2009) and in CAMPOS-DA-PAZ et al. (*Mol. Biotechnol.*, vol. 39(2), p: 155-8, 2008).

The nucleic acid coding for the immunocytokine of the invention may be delivered in vivo alone or in association with a vector.

In a third aspect, the present invention relates to a vector comprising a nucleic acid as described above.

In its broadest sense, a "vector" is any vehicle capable of facilitating the transfer of the nucleic acid coding for the immunocytokine of the invention to the cells. Preferably, the vector transports the nucleic acid to cells with reduced degradation relative to the extent of degradation that would result in the absence of the vector. In general, the vectors useful in the invention include, but are not limited to, plasmids, cosmids, phagmids, episomes, artificial chromosomes, viruses, other vehicles derived from viral or bacterial sources that have been manipulated by the insertion or incorporation of the immunocytokine nucleic acid sequences.

Plasmid vectors are a preferred type of vector and have been extensively described in the art and are well known to those of skill in the art. See e.g., SANBROOK et al., "Molecular Cloning: A Laboratory Manual," Second Edition, Cold Spring Harbor Laboratory Press, 1989. Not limiting examples of plasmids include pBR322, pUC18, pUC19, pRC/CMV, SV40, and pBlueScript, and other plasmids are well known to those of ordinary skill in the art. Additionally, plasmids may be custom designed using restriction enzymes and ligation reactions to remove and add specific fragments of DNA.

Preferably, the nucleic acid vector can include selectable markers that are active both in bacteria and in mammalian cells.

In a forth aspect, the present invention relates to a host cell genetically engineered with the nucleic acid or with the vector described previously.

As used herein, the term "host cell genetically engineered" relates to host cells which have been transduced, transformed or transfected with the nucleic acid or with the vector described previously.

As representative examples of appropriate host cells, one can cite bacterial cells, such as *E. coli*, fungal cells such as yeast, insect cells such as Sf9, animal cells such as CHO or COS, plant cells, etc. The selection of an appropriate host is deemed to be within the scope of those skilled in the art from the teachings herein.

Preferably, the host cell genetically engineered is an animal cell, and most preferably CHO-S cell (INVITROGEN, cat No 11619-012).

Chinese hamster ovary (CHO) cells are frequently used in the biopharmaceutical industry for the manufacture of biologics such as recombinant proteins, antibodies, peptibodies, and receptor ligands. One of the reasons that CHO cells are often used is that these cells have an extensive safety track record for biologics production. This is considered to be a well-characterized cell line and, as a result, the safety testing required may be less rigorous in some respects (e.g., retroviral safety) than that required for other cell types. Nevertheless, the production of interleukin 15 is very difficult, especially in this cell.

Surprisingly, the inventors established that the immunocytokines of the invention are well produced in this cell, the obtained immunocytokines having further a very good purity and activity.

The introduction of the nucleic acid or of the vector described previously into the host cell can be done by methods well known from one of skill in the art such as calcium phosphate transfection, DEAE-Dextran mediated transfection, or electroporation.

The present invention also relates to a method of producing a host cell genetically engineered expressing an immunocytokine according to the invention, said method comprising the steps of: (i) introducing in vitro or ex vivo a nucleic acid or a vector as described above into a host cell, (ii) culturing in vitro or ex vivo the recombinant host cell genetically engineered obtained and (iii), optionally, selecting the cells which express and/or secrete said immunocytokine. Such recombinant host cells can be used for the production of immunocytokine of the invention.

Pharmaceutical Composition Comprising the Immunocytokine of the Invention

A further object of the invention relates to a pharmaceutical composition comprising the immunocytokine as described above, a nucleic acid encoding thereof, or a vector comprising said nucleic acid, eventually associated with a pharmaceutically acceptable carrier.

The expression "pharmaceutically acceptable" refers to molecular entities and compositions that are physiologically tolerable and do not typically produce allergic or similar undesirable reactions, such as gastric upset, dizziness and the like when administered to a human. Preferably, as used herein, the expression "pharmaceutically acceptable" means approvable by a regulatory agency of the Federal or state government or listed in the U.S. Pharmacopeia or other generally recognized pharmacopeia for use in animals, and more particularly in humans.

The term "carrier" refers to a solvent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like.

The pharmaceutical composition comprises an "effective amount" of the immunocytokine of the invention, which effective amount is sufficient to inhibit the growth of cancer cells, preferably sufficient to induce the regression of tumor growth. The doses used for the administration can be adapted as a function of various parameters, in particular as a function of the mode of administration used, of the relevant pathology, or alternatively of the desired duration of treatment. Naturally, the form of the pharmaceutical composition, the route of administration, the dosage and the regimen naturally depend on the condition to be treated, the severity of the illness, the age, weight, and sex of the subject, etc. The ranges of effective doses provided below are not intended to limit the invention and represent preferred dose ranges. However, the preferred dose can be tailored to the individual subject, as is understood and determinable by one of skill in the art, without undue experimentation.

In view of the marked efficiency of the immunocytokine of the invention, the skilled person can plan to use very small doses for treating a subject. As a non limiting example, the immunocytokine of the invention can be can be administered by injection at a dose of 2.5 mg/kg or 1 mg/kg of subject or less, preferably at a dose of 0.5 mg/kg or less or 0.25 mg/kg or less and most preferably at a dose of 0.1 mg/kg or less.

As an example, the pharmaceutical compositions of the invention can be formulated for topical, oral, intranasal, intraocular, intravenous, intramuscular or subcutaneous administrations and the like. Preferably, the pharmaceutical composition contains vehicles which are pharmaceutically acceptable for a formulation intended to be injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. Suitable pharmaceutical carriers are described in "Remington's Pharmaceutical Sciences" by E. W. Martin.

The immunocytokine of the invention, nucleic acids coding therefore or nucleic acid vectors may be solubilized in a buffer or water or incorporated in emulsions, microemulsions, hydrogels (e.g. PLGA-PEG-PLGA triblock copolymers-based hydrogels), in microspheres, in nanospheres, in microparticles, in nanoparticles (e.g. poly(lactic-co-glycolic acid) microparticles (e.g. poly lactic acid (PLA); poly (lactide-co-glycolic acid) (PLGA); polyglutamate microspheres, nanospheres, microparticles or nanoparticles), in liposomes, or other galenic formulations. In all cases, the formulation must be sterile and fluid to the extent of acceptable syringability. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose.

Dispersions can also be prepared in glycerol, liquid polyethylene glycols, mixtures thereof and in oils. Under ordinary conditions of storage and use, these preparations contain a preservative to prevent the growth of microorganisms.

The immunocytokines according to the invention can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or a dispersion medium containing, for example, water, ethanol, polyol (for example, glycerol, propylene glycol, and liquid polyethylene glycol, and the like), suitable mixtures thereof, and vegetables oils. The immunocytokines of the invention may also be modified, by pegylation as an example, so as to increase its biodisponibility. When the immonocytokine of the invention has a nucleic acid form, the carrier can also be a vector, such as a virus (e.g. MVA, rAAV, lentivirus, etc.)

The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate, gelatin, polyols, half-life enhancing covalent and non covalent formulations.

There are numerous causes of peptide instability or degradation, including hydrolysis and denaturation. Hydrophobic interaction may cause clumping of molecules together (i.e. aggregation). Stabilizers may be added to reduce or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from ionic and non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycrol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

The promise of cytokine therapy does indeed derive from the identification of these novel cytokines but even more fundamentally, the field is greatly benefiting from the ever-expanding amount of preclinical data that convincingly demonstrate synergistic and/or novel biologic effects, which may be achieved through the use of several combinations of cytokines with complementary immune-stimulating capabilities. Potential therapeutic active agent combinations with RLI-based immunocytokines includes by example chemotherapeutic agents, antiangiogenic agents, or immunomodulatory agents.

In a preferred embodiment, the composition of the invention may comprise a further therapeutic active agent, such as chemotherapeutic agents, antiangiogenic agents, or immunomodulatory agents.

For chemotherapeutic agents, it has been demonstrated that their therapeutic effects could be mediated in part by an indirect effect on immune responses, either by inducing an immunogenic cell death, balancing the immunosuppressive environments, debulking the primary large tumor and then facilitating the immune attack or by inducing a transient lymphopenia followed by homeostatic lymphoproliferation. Many of them are well known from the skilled person and, and as an example of chemotherapeutic agent which can be combined with the immunocytokine of the invention, on can cite fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbizine, etoposide, teniposide, campathecins, bleomycin, doxorubicin, idarubicin, daunorubicin, dactinomycin, plicamycin, mitoxantrone, L-asparaginase, doxorubicin, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, topotecan, kinase inhibitors, phosphatase inhibitors, ATPase inhibitors, tyrphostins, protease inhibitors, inhibitors herbimycm A, genistein, erbstatin, and lavendustin A.

For antiangiogenic agents, it has been demonstrated that they have off-target effects on immune system and then could facilitate the tumor immune responses. As an example of antiangiogenic agent which can be combined with the immunocytokine of the invention, on can cite drugs targeting the vascular endothelial growth factor receptor (VEGFR) via its tyrosine kinase, such as sorafenib, sunitinib, and pazopanib, or the mammalian target of rapamycin (mTOR), such as temsirolimus and everolimus.

For immunomodulatory agents which can be combined with the immunocytokine of the invention, one can cite cytokines (IL-2, IL-7, IL-15, IL-12, IL18, IL-21, GM-CSF, G-CSF, IFNα, . . . ), chemokines/antiangiogenic cytokines (IP10, Mig, SDF-1, RANTES, . . . ), TLR agonists, and immunoregulatory antibodies (anti-CTLA4, anti-PD1, anti-TGFb, agonist anti-CD40, . . . ).

Therapeutic Methods and Uses

In a further aspect, the present invention relates to a pharmaceutical composition as described previously for treating cancer in a subject, preferably of a pharmaceutical composition comprising an immunocytokine as described previously.

As used herein, the term "subject" denotes a mammal, such as a rodent, a feline, a canine or a primate, and most preferably a human.

In another aspect, the present invention relates to products containing:

(i) an immunocytokine as describe above, a nucleic acid sequence coding therefore, or a vector comprising such a nucleic acid sequence, and (ii) a therapeutic agent, preferably an anticancer agent, as a combined preparation for simultaneous, separate, or sequential use for treating cancer in a subject.

In still another aspect, the present invention relates to a method for treating cancer in a subject comprising the step of administrating to said subject a pharmaceutical composition as described previously.

In a final aspect, the present invention relates to a method for treating cancer comprising the step of simultaneously, separately, or sequentially administrating to a subject in need thereof of a therapeutically effective amount of:

(i) an immunocytokine as describe above, a nucleic acid sequence coding therefore, or a vector comprising such a nucleic acid sequence, and (ii) a therapeutic agent, preferably an anticancer agent.

In the context of the invention, the term "treating" or "treatment", as used herein, means reversing, alleviating, inhibiting the progress of, or preventing the disorder or condition to which such term applies, or one or more symptoms of such disorder or condition. The term "treating cancer" as used herein means the inhibition of the growth of cancer cells. Preferably such treatment also leads to the regression of tumor growth, i.e., the decrease in size of a measurable tumor. Most preferably, such treatment leads to the complete regression of the tumor.

In the following, the invention is described in more detail with reference to amino acid sequences, nucleic acid sequences and examples. However, no limitation of the invention is intended by the details of the examples. Rather, the invention pertains to any embodiment which comprises details which are not explicitly mentioned in the examples herein, but which the skilled person finds without undue effort.

EXAMPLES

1) Construction of Interleukin 15 Based Immunocytokines

Construction of Anti-CD20 (Rituximab) and Anti-GD2-O-Acetylated Immunocytokines

The expression plasmids encoding for the anti-CD20 chimeric IgG light chains and anti-GD2-O-acetylated chimeric IgG light chains were kindly provided by Dr WATIER (Université François-Rabelais de Tours, France) and Dr BIRKLE (INSERM, Université de Nantes, U892, France) respectively. The chimeric IgG heavy chain sequences of each antibody were designed to be fused in 3'term with or without a linker of 22 amino-acid (SEQ ID NO:16) to IL15 (SEQ ID NO:3, wherein the amino acid at position 93 is K). These nucleotide sequences were synthesized and cloned in pcDNA3.1 plasmids by GENEART. The complete sequence of light and heavy chains of the anti-GD2-O-acetylated antibody (8B6) are disclosed in the patent application EP 2,076,542 A1 and in CERATO et al. (*Hybridoma*, vol. 16(4), p: 307-16, 1997). The complete sequence of light and heavy chains of the anti-CD20 antibody (2B8) are disclosed in the U.S. Pat. No. 5,736,137 (ANDERSON et al. as the antibody called "C2B8") and in REFF et al. (*Blood*, vol. 83(2), p: 435-45, 1994).

Plasmid DNA Preparation and Transfection Reagent

A 40 kDa linear PEI was obtained from POLYSCIENCE. A 1 mg/mL stock solution was prepared by dissolving the PEI in water with heating, neutralizing by NaOH, and sterilizing by filtration through a 0.22 μm filter. The solution stock was aliquoted and stored at −20° C.

Plasmids DNA for transfections were purified using the plasmid purification kits following the manufacturer's protocol (MACHEREY-NAGEL) and sterilizing by filtration through a 0.22 μm filter.

Production and Purification of the Immunocytokines

1-Transient Transfection in Suspension:

Routinely maintained CHO-S (INVITROGEN) cells were seeded at a density of $1 \times 10^6$ cells/mL in POWERCHO™-2 Medium (LONZA) and cultured overnight at 37° C. in a shaking incubator (100 rpm) with 5% $CO_2$. For transfection, cells were then diluted to $2 \times 10^6$ cells/mL in CD-CHO medium (INVITROGEN). The transfection complexes were prepared in 10% of the culture volume using NaCl 150 mM. Expression constructs DNA (2.5 mg/L of culture volume, using a 1:2 ration of plasmid encoding heavy chain to plasmid encoding light chain) were mixed with PEI diluted in NaCl (10 mg/L of final culture volume) and incubated for 10 min at room temperature before adding to the culture. Cells were cultured in a shaking incubator (130 rpm) at 37° C. for 5 h before doubling the culture volume with Power-CHO2 medium. Supernatant were collected 5 days postransfection.

2-Stable Transfection on Adherent Cells

CHO-K1 cells (ATCC n° CCL-61) were grown in DMEM supplemented with 1-glutamine, 10% FCS and penicillin (100 units/ml)/streptomycin (100 μg/ml) and transfected with each vector using LIPOFECTAMINE™ 2000 reagent (INVITROGEN), as recommended by the manufacturer. Clones were selected by limit dilution with medium containing geneticin and hygromycin (0.5 mg/ml) or blasticin and hygromycin (5 μg/mL and 100 μg/mL) for the anti-GD2O-aceylated ICK and anti-CD20 ICK, respectively. Culture supernatant of each clone was assayed for bifunctional proteins production by ELISA. For the production of ICK, selected clones were amplified in 25% DMEM medium and 75% AIM™ medium (INVITROGEN). Cells were then maintained in 100% of AIM™, and supernatant were collected and replaced every 2 days, for 10 days.

3-Supernatant Purification:

Collected supernatant were centrifuged at 3000 rpm for 20 minutes at 4° C., equilibrated at pH 7.8 with NaOH and filtered through a 0.22 μm filter. The conditioned mediums were purified by affinity chromatography using a protein A column (GE) according to the manufacturer's instructions. The purified proteins were concentrated with a 50 kDa AMICON™ units (MILLIPORE). During this step, elution buffer was replaced by PBS. The Purified proteins were finally assayed by ELISA and absorbance measuring at 280 nm. Purity was evaluated by electrophoresis.

4-Detection of the Immunoglobulin Moiety by ELISA.

MAXISORP™ flat bottom microtiter plate (NUNC) was coated with 100 μL of goat anti-human antibody (UP892370, INTERCHIM) diluted in PBS to 1.5 μg/mL for h at 4° C. Plate was then blocked with 200 μL of blocking buffer (1% BSA+ 0.1% TWEEN™ 20 in PBS) for 1 h at 37° C. Plate was then washed 3 times with washing buffer (0.1% TWEEN™ 20 in PBS) and sample diluted in blocking buffer were added and incubated 30 min at 37° C. (100 μL). After 3 washing, Peroxidase conjugated goat anti-human IgG1 (109-036-003, JACKSON) diluted 1:10000 was added and incubated for 30 min at 37° C. TMB substrate (INTERCHIM) was used to determine protein levels and plates were read at 450 nm. Purified Rituximab (ROCHE) was used to generate a standard curve on plate.

5-Detection of the Cytokine Moiety by ELISA.

MAXISORP™ flat bottom microtiter plate (NUNC) was coated with 100 μL of the anti-IL15 B-E29 (DIACLONE) diluted in carbonate buffer to 2 μg/mL for 16 h at 4° C. Plate was then blocked with 200 μL of blocking buffer (1% BSA in PBS) for 1 h at 37° C. the plate was then washed 3 times with washing buffer (0.05% Tween™ 20 in PBS). Sample diluted in TBS+0.05% BSA were added and incubated 1 h 30 min at 37° C. (100 μL). After 3 washing, biotinylated anti-IL15 antibody BAM 247 (R&D SYSTEM) diluted to 200 ng/mL was added and incubated for 1 h 30 min at 37° C. The plate was washed 3 times and peroxidase conjugated streptavidin was added dilution 1:1000. TMB substrate (INTERCHIM) was used to determine protein levels and plates were read at 450 nm. IL-15 (PEPROTECH) was used to generate a standard curve on plate.

The results have shown that the obtained preparation of immunocytokines comprises many protein contaminants (i.e. equal or superior to 25%). So as to reduce these protein contaminations, the two anti-GD2-O-acetylated/interleukin 15 immunocytokines have been subjected to another round of protein A SEPHAROSE™ purification.

After this second round of protein A SEPHAROSE™ purification, the purity of the ICK c8B6-122-IL15 and c8B6-IL15 was respectively of 70 and 90%.

Proliferation Activity of the Immunocytokines

The interleukin-15 proliferation activity of the obtained immunocytokines was tested. The proliferative responses of Kit 225 and 32Dß cells to ICK were measured by [$^3$H] thymidine incorporation. Cells were maintained in culture medium for 3 days, washed twice, and starved in medium without cytokine for 24 h or 4 h for Kit 225 and 32Dß, respectively. They were then seeded in multiwell plates at $10^4$ cells/well in 100 µl and cultured for 48 h in medium supplemented with increasing concentration of sample. Human rIL-15 and RLI were used as calibrator. Cells were pulsed for 16 h with 0.5 µCi/well of [$^3$H] thymidine, harvested onto glass fiber filters, and cell-associated radioactivity was measured.

The FIG. 1 shows [$^3$H]Thymidine incorporation by Kit 225 and 32Dß cells cultured with increasing concentrations of rIL-15 (■), c8B6-IL15 (Δ), and c8B6-122-IL15 (○).

Figure 2:
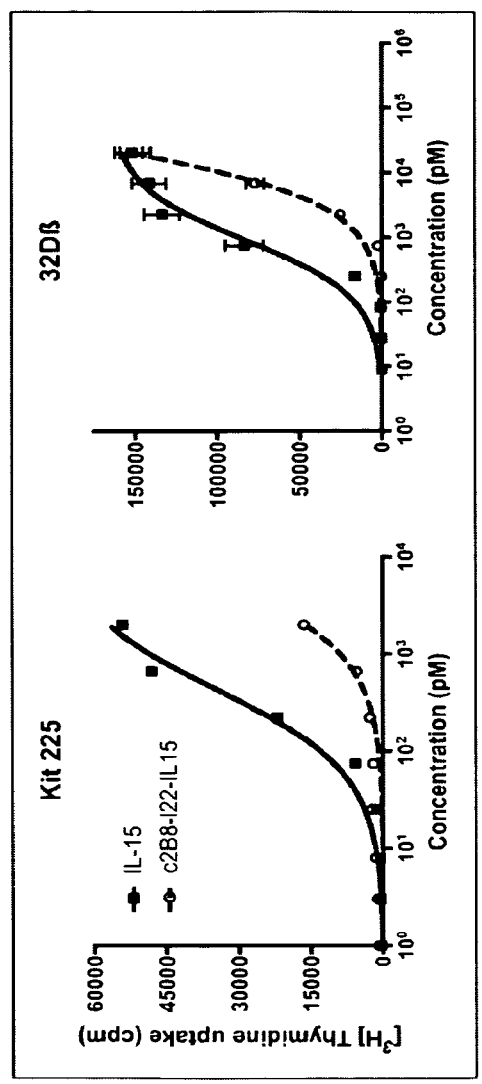
FIG. 2 shows the activity of IL15 anti-GD2-O-acetylated immunocytokine as compared to IL 15.

The FIG. 2 shows [$^3$H]Thymidine incorporation by Kit 225 and 32Dß cells cultured with increasing concentrations of rIL-15 and c2B8-122-IL15 (○).

The results show that the biological activity of IL-15 is drastically decreased in the context of immunocytokine, meaning that conjugation of IL-15 with monoclonal antibody induces a loss of activity. Moreover, this loss is more important in absence of linker between the two moieties. It is to be noted that this loss of activity is more pronounced in the βγ context.

Binding Activity of the Immunocytokines

The specific binding of the anti-CD20 and anti-GD2 O-acetylated ICK were was assessed by flow cytometry on tumors cells Raji and IMR32 respectively. The capacity of ICK to bind IL-15 receptor on effector cells were tested on Kit225. ICK coated on targeted cells were revealed with a PE-conjugated goat anti-human IgG mAb (PN IM0550, BECKMAN COULTER), or with a biotinylated mouse anti-IL15 antibody (BAM247, R&D SYSTEM) coupled to PE-streptavidin (SIGMA-ALDRICH). Targeted cells ($1\times10^5$) were incubated with each ICK for 1 h at 4° C., washed and then incubated with a PE-conjugate for 1 h at 4° C. Washed cells were finally analyzed on a FACSCALIBUR™ (BECTON DICKINSON).

Figure 3:
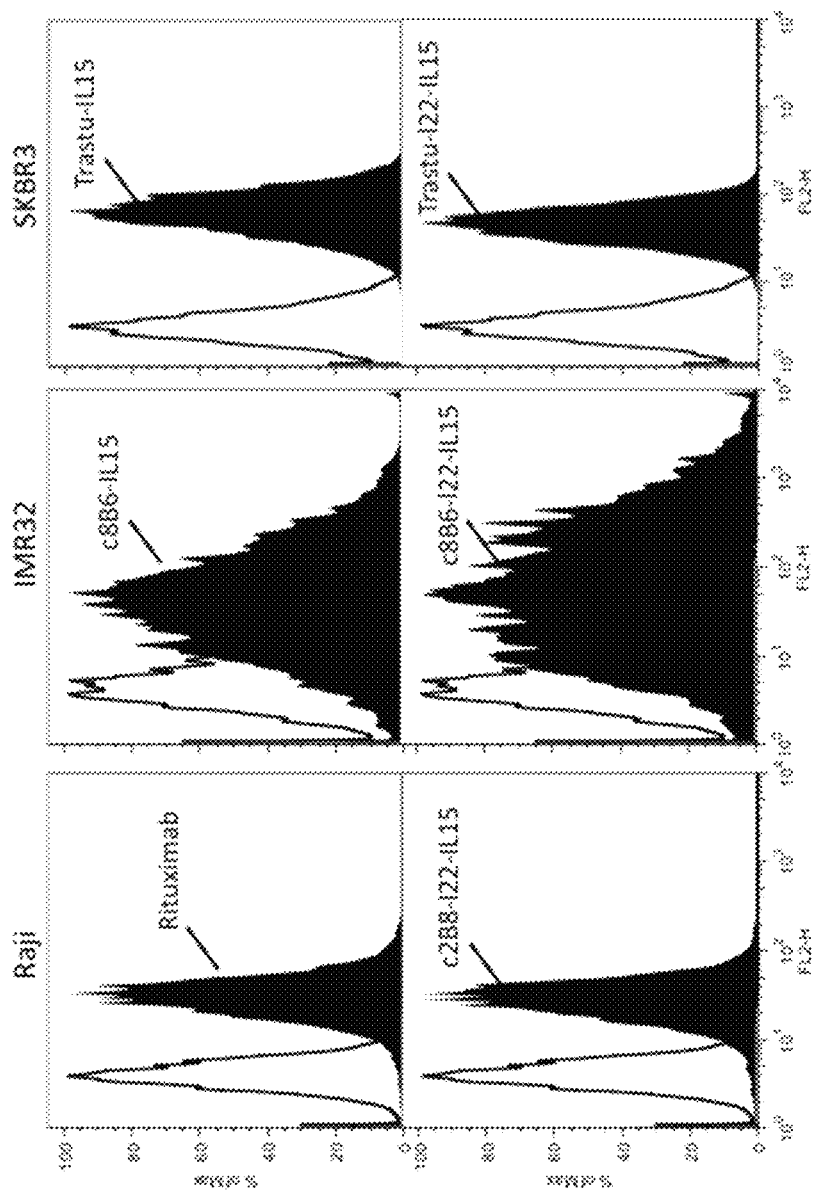
FIG. 3 shows the CD20, GD2-Oacetylated and HER-2 binding activity of IL15 anti-CD20, anti-GD2-O-acetylated and anti-HER2 IL-15 immunocytokines respectively.

FIG. 3 shows flow cytometry evaluation of the ICK anti-CD20 (c2B8-122-IL15) and anti-GD2O-acetylated (c8B6-IL15 and c8B6-122-IL15) on CD20 expressing Raji cells and GD2O-acetylated expressing IMR32 cells. Cells were first incubated with ICK, then with a PE-conjugated goat anti-human IgG mAb for anti-CD20 or with biotinylated anti-IL15+PE-conjugated streptavidin for anti-CD20 and anti-GD2, respectively. Finally sample were analysed on a FACSCALIBUR™. ICK were compared on Raji cells to the anti-CD20 Mab Rituximab (MABTHERA™, ROCHE).

Figure 4:
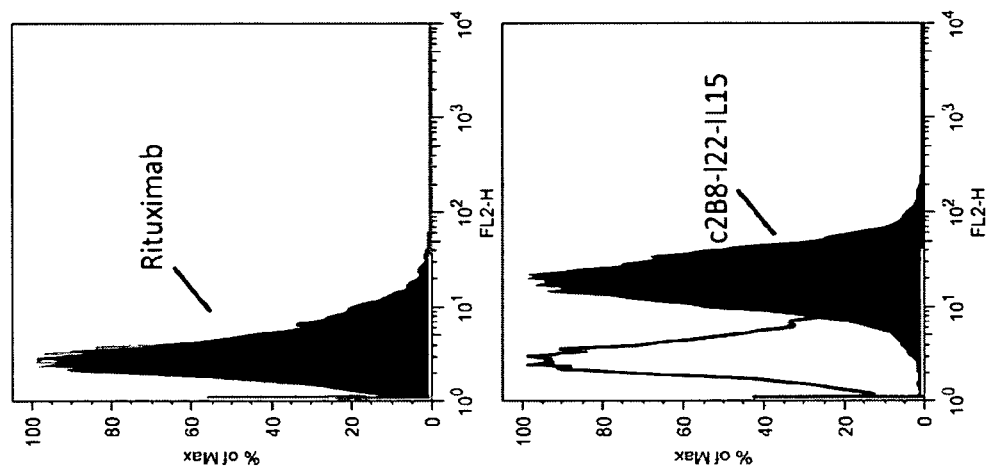
FIG. 4 shows the IL-15Rα binding activity of IL15 anti-CD20 immunocytokine as compared to anti-CD20 antibody (Rituximab).

FIG. 4 shows flow cytometry evaluation of the ICK anti-CD20 (c2B8-122-IL15 and anti-GD2O-acetylated (c8B6-IL15 and c8B6-122-IL15) on IL15R expressing Kit 225 cells. Cells were first incubated with ICK, then with a PE-conjugated goat anti-human IgG mAb. Finally sample were analysed on a FACSCALIBUR™. ICK were compared to the anti-CD20 Mab Rituximab (MABTHERA™, ROCHE).

The results show that the different immunocytokines bind to the IL-15 receptor and also to their respective tumor antigen target.

Thus, the loss of interleukin 15 activity in these immunocytokines is not the result of a loss of the binding of interleukin 15 on its specific receptor. Nevertheless, it appears that this existing binding does not permit to induce a normal cell proliferation Construction of RLI-Based Immunocytokines Construction of Anti-CD20 and Anti-GD2-O-Acetylated RLI Immunocytokines The anti-CD20 and anti-GD2-O-acetylated immunocytokines were constructed as previously excepted that the IL15 *Homo sapiens* sequence was replaced by RLI2 sequence (SEQ ID NO: 17).

Production and Purification of the Immunocytokines

The production and purification of the immunocytokines were done as previously disclosed except that these immunocytokines were obtained with good yields and good purity (i.e. greater than 90%) after only one round of protein A SEPHAROSE™ purification.

Binding Activity of the Immunocytokines

The specific binding of the anti-CD20 and anti-GD2 O-acetylated ICK RLI were was assessed by flow cytometry on tumors cells Raji, WM266.4 and IMR32. The capacity of ICK RLI to bind IL-15 receptor on effector cells were tested on Kit225. ICK RLI coated on targeted cells were revealed cells with a PE-conjugated goat anti-human IgG mAb (PN IM0550 BECKMAN COULTER), or with a biotinylated mouse anti-IL15 antibody (BAM247, R&D SYSTEM) coupled to PE-streptavidin (SIGMA-ALDRICH). Targeted cells ($1\times10^5$) were incubated with each ICK for 1 h at 4° C., washed and then incubated with a PE-conjugate for 1 h at 4° C. Washed cells were finally analyzed on a FACSCALIBUR™ (BECTON DICKINSON).

Figure 5:
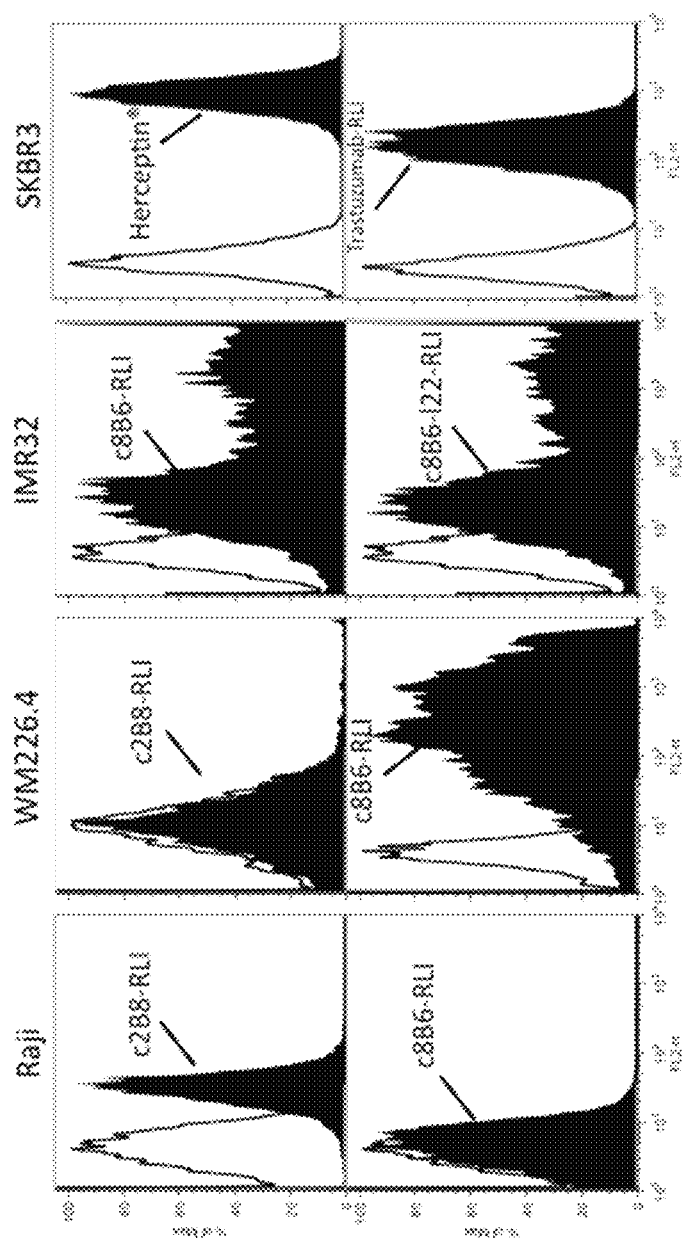
FIG. 5 shows the CD20, GD2-Oacetylated and HER-2 binding activity of IL15 anti-CD20, anti-GD2-O-acetylated and anti-HER2 RLI immunocytokines respectively.

FIG. 5 shows flow cytometry evaluation of the ICK c2B8-RLI, c8B6-RLI and c8B6-122-RLI on CD20 expressing Raji cells and GD2O-acetylated expressing WM266.4 and IMR32 cells. Cells were first incubated with ICK RLI, then with a PE-conjugated goat anti-human IgG mAb for anti-CD20 or with biotinylated anti-IL15+PE-conjugated streptavidin for anti-CD20 and anti-GD2O-acetylated, respectively. Finally, samples were analysed on a FACSCALIBUR. ICK RLI were compared on Raji cells to the anti-CD20 Mab Rituximab (MABTHERA, ROCHE).

Figure 6:
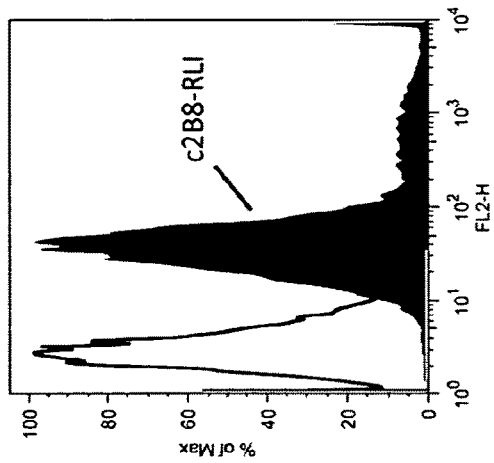
FIG. 6 show the IL15Rα binding activity of RLI anti-CD20 and IL15 anti-GD2-O-acetylated immunocytokines.
Figure 6:
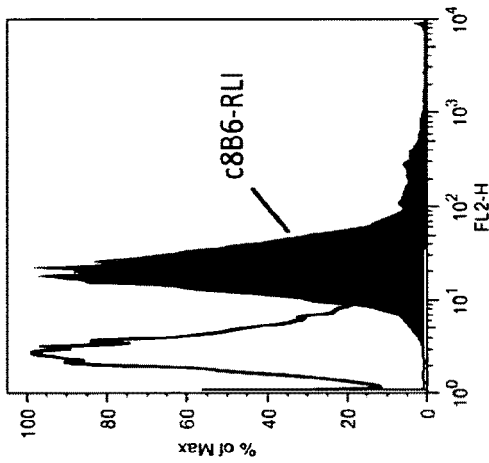

FIG. 6 shows flow cytometry evaluation of the ICK RLI anti-CD20 (c2B8-RLI) and anti-GD2O-acetylated (c8B6-RLI and c8B6-122-RLI) on IL15Rα expressing Kit 225 cells. Cells were first incubated with ICK RLI, then with a PE-conjugated goat anti-human IgG mAb. Finally, sample were analysed on a FACSCALIBUR™.

The results show that the immunocytokines of the invention bind to the IL-15 receptor and also to their respective tumor antigen target.

Proliferation Activity of the Immunocytokines

The interleukin-15 proliferation activity of the newly obtained immunocytokines was tested.

Figure 7:
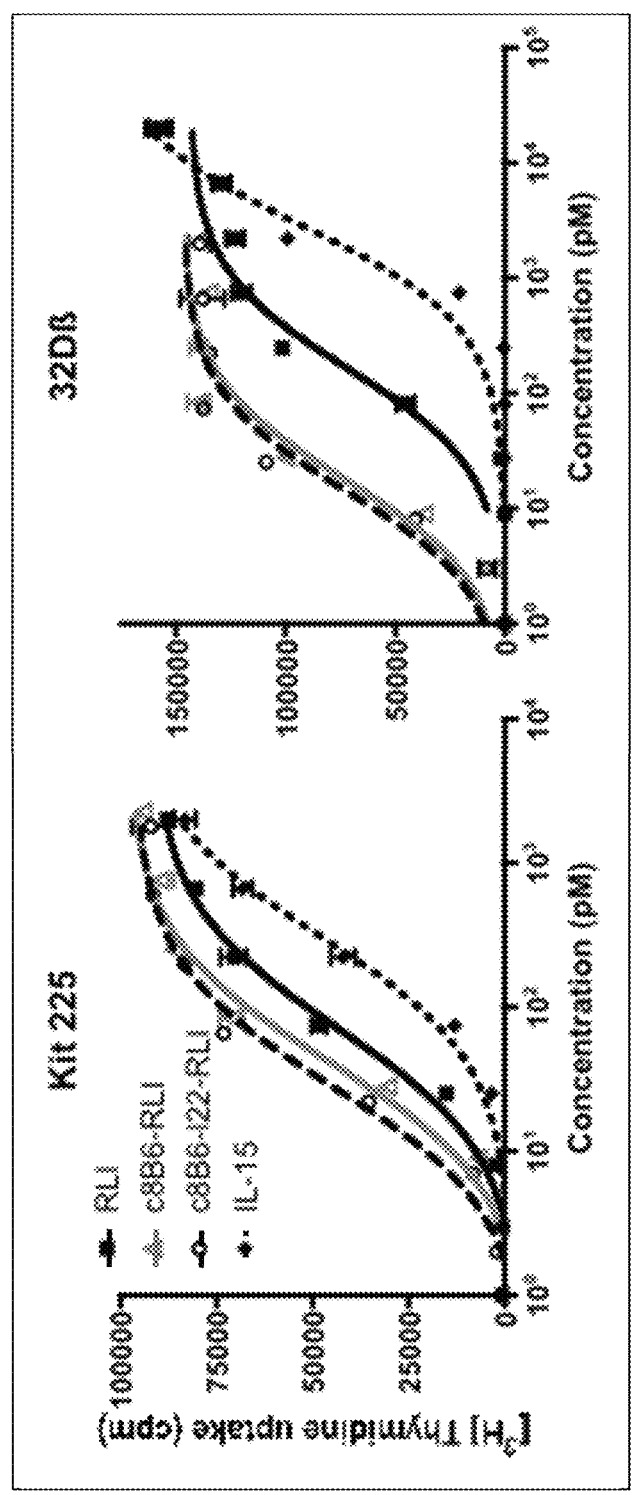
FIG. 7 shows the activity of RLI anti-CD20 immunocytokines as compared to IL15.

The FIG. 7 shows [$^3$H]Thymidine incorporation by Kit 225 and 32Dß cells cultured with increasing concentrations of RLI (■), rIL-15 (♦) c8B6-RLI (Δ), and c8B6-122-RLI (○).

Figure 8:
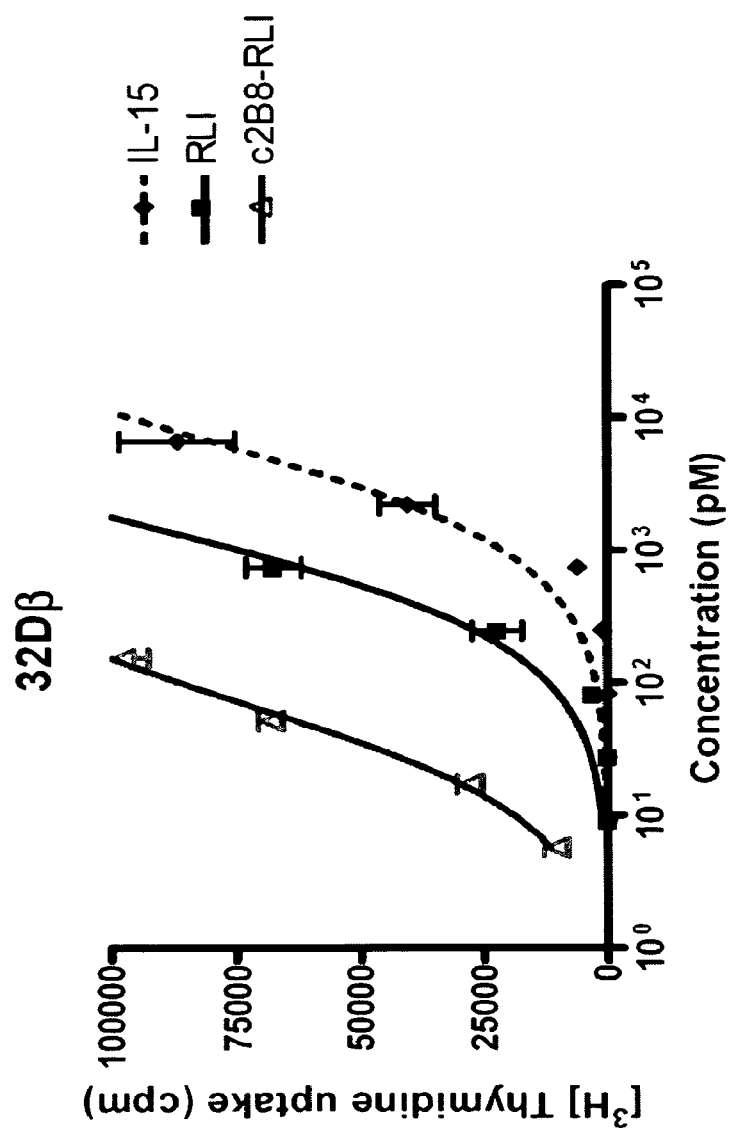
FIG. 8 shows the activity of RLI anti-GD2-O-acetylated immunocytokines as compared to IL 15.

The FIG. 8 shows [$^3$H]Thymidine incorporation by 32Dß cells cultured with increasing concentrations of RLI (■), rIL-15 (♦) and c2B8-RLI (Δ).

The results show that the biological activity of IL-15 is conserved in the context of RLI-derived immunocytokines despite IL15 immunocytokines, meaning that conjugation of RLI with a monoclonal antibody permits surprisingly the conservation of this IL-15 activity. Moreover, this intriguing effect does not require any second linker between RLI and the monoclonal antibody. Surprisingly, it is to be noted that the RLI-derived immunocytokines present a significant gain of biological activity as compared to free IL-15 in the βγ context (about 10 to 100 fold increase).

Antitumor Capability of the Anti-GD2-O-Acetylated Immunocytokine

The murine NXS2 neuroblatomas cell line was propagated in DMEM (10% FCS) under standard tissue culture conditions (37° C., 5% CO2). The NXS2 NB cell line expressing GD2-O-Ac was developed and characterized by LODE et al. (*J Natl. Cancer Inst.*, vol. 89(21), p: 1586-94, 1997).

A/JOlaHsd mice, aged of 8 weeks, were purchased from HARLAN laboratories. Mice were housed at the animal facility of Inserm U892, which is approved by the French Association for Accreditation of Animal Care Laboratories and is maintained in accordance with the regulations and standards of Inserm Institute and the French Department of Agriculture.

Experimental hepatic metastases were induced by tail vein injection of $1 \times 10^5$ NXS2 NB tumor cells in 200 μl of DMEM (pH 7.4). Treatment was initiated one day after tumor cell inoculation and consisted of 4 i.p. injections of 80 pmol of c8B6-RLI2 or c8B6 on day 1, 4, 7 and 11. Mice were sacrificed 25 days after graft and the hepatic tumor burden was evaluated by wet liver weight.

Figure 9:
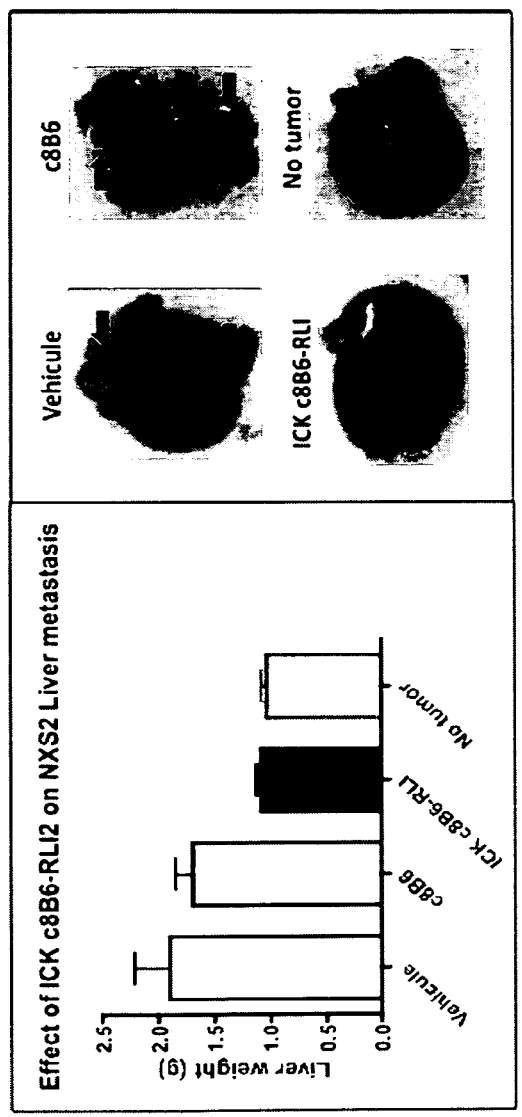
FIG. 9 shows the anti-metastatic activity of anti-GD2-O acetylated immunocytokine as compared to anti-GD2-O acetylated antibody.

The FIG. 9 shows the efficacy of c8B6-RLI2 on NXS2 liver metastasis. c8B6 (12 μg) or c8B6-RLI (16 μg) was administered i.p. on days 1, 4, 7, and 11. Left: Graph represents mean of each group (n=5); bars, SEM. Right: representative pictures of liver, Arrows indicate some metastasis.

The results show that the mice which have received ICK remain liver metastasis free. Thus, and contrary to c8B6, ICK can eradicate the development of NXS2 liver metastasis, meaning that RLI conjugation to a monoclonal antibody dramatically enhances its antitumor capabilities.

Antitumor Capability of the Anti-CD20-RLI2 in Raji Model:

The human Raji B cells were cultured in RPMI1640 medium supplemented with 10% fetal calf serum, 2 mM l-glutamine.

SCID CB-17 mice, aged 8 weeks, were purchased from the CHARLES RIVER Breeding Laboratories. Mice were kept under specific pathogen-free conditions in a separate facility using autoclaved cages of micro-isolator units and fed with irradiated solid food and sterilised water.

For inoculation, Raji cells were harvested in their log-phase, washed and re-suspended at $2.5 \times 10^6$ cells/0.1 ml in phosphate-buffered saline (PBS) before being injected intravenously into the mice followed by ip treatment with immunocytokines 3 times a week (beginning on day 5) for 3 week after implantation. Mice received treatment in equimolar quantity except for the groups "immunocytokine" and "rituximab+RLI" which received a half dose. The mice were monitored daily for the presence of hind-leg paralysis and in that case sacrificed and scored as dead.

Figure 10:
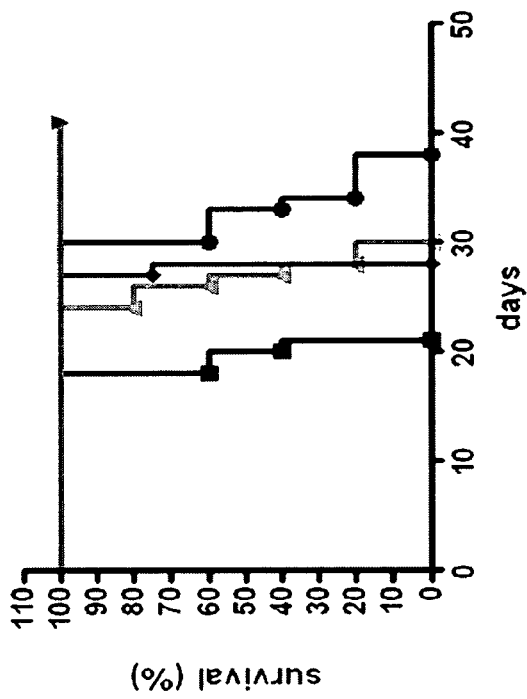
FIG. 10 shows the antitumor activity of anti-CD20 immunocytokine in Raji model.

The FIG. 10 show the Kaplan-Meier survival analysis of CB17 SCID mice iv injected with Raji cells (n=5) and treated on J5-J7-J9; J12-J14-J16; J19-J21-J23 with PBS (■); RLI (▲; 2 μg); Rituximab (♦; 12 μg); Rituximab+RLI (•; 6 μg+1 μg), antiCD20-RLI (▼; 8 μg).

The results shows that the percentage of survival obtained in the Raji mice treated with RLI or with rituximab was similar and extend the 50% survival of tumour bearing mice from 20 to 27 days and to 28 days respectively relative to the PBS control.

The results show a further half increase of of the percentage of survival of tumour bearing mice for the "Rituximab+RLI" group, which increase is significantly different from the one obtained in the RLI group ($P<0.01$ or less).

Finally and surprisingly, the results show that the treatment with anti-CD20 immunocytokine totally abrogates tumor development with no mouse death at the end of the experiment (day 50).

3) Construction of Further Immunocytokines

Construction of Anti-HER2Neu (Full IgG and ScFv) RLI and IL15 Immunocytokines

Sequence encoding for the anti-HER2 murine 4D5 IgG light chains, anti-HER2 murine IgG 4D5 heavy chains and anti-HER2 scFv were kindly provided by Dr DONDA (Biochemistry Institute Lausanne, Switzerland). The anti-HER2Neu IL15- and RLI-immunocytokines were constructed as previously on the basis of the anti HER2Neu light (SEQ ID NO:18) and heavy (SEQ ID NO:19) chains of the anti-HER2Neu antibody. For these constructions, sequence encoding the leader sequence of beta2 microglobulin in frame with sequence encoding chimeric IgG heavy chain sequences were designed to be fused in 3'term with or without a linker of 22 amino-acid (SEQ ID NO:16) to IL15 (SEQ ID NO:20 and 21 respectively) and to RLI (SEQ ID NO:22 and 23 respectively).

Constructions corresponding to sequence encoding the leader sequence of beta2 microglobulin in frame with sequence encoding anti-HER2Neu ScFv fragment fused in 3'term with or without a linker of 22 amino-acid to IL15 (SEQ ID NO:24 and 25 respectively) and to RLI (SEQ ID NO:26 and 27 respectively) were further designed and produced. These nucleotide sequences were synthesized by GENEART and sub-cloned in pCR3 (INVITROGEN) plasmids Biological and binding activities of these compounds are tested.

Construction of Interleukin 15 Based Immunocytokines

Plasmid DNA Preparation and Transfection Reagent

A 40 kDa linear PEI was obtained from POLYSCIENCE. A 1 mg/mL stock solution was prepared by dissolving the PEI in water with heating, neutralizing by NaOH, and sterilizing by filtration through a 0.22 μm filter. The solution stock was aliquoted and stored at −20° C.

Plasmids DNA for transfections were purified using the plasmid purification kits following the manufacturer's protocol (MACHEREY-NAGEL) and sterilizing by filtration through a 0.22 μm filter.

Production and Purification of the Immunocytokines

1-Transient Transfection:

HEK293T cells, kindly provided by Dr. SCHNEIDER (Biochemistry Institute Lausanne, Switzerland) were seeded in T175 cm2 flask in DMEM-GLUTAMAX™ 10% SVF at 37° C. and 5% $CO_2$. The day of transfection, a complex of DNA plasmid and PEI were prepared in sterile NaCl 150 mM. Plasmid DNA diluted in NaCl (1.25 mg/L of culture volume) were mixed with PEI diluted in NaCl (12.5 mg/L of culture volume) and incubated for 10 min at room temperature before adding to the cell culture. For anti-HER2 IgG-RLI or -IL15 immunocytokine a ratio of 1:2 DNA plasmid (heavy:light chain) were used. Cells were then cultured at 37° C. for 4 h. After this time medium was removed and fresh DMEN without SVF was added. Supernatant were collected 5 days postransfection.

2-Supernatant Purification:

Collected supernatant were centrifuged first at 1000 rpm for 5 minutes and secondly at 3000 rpm for 15 minutes at 4° C., adjusted to 20 mM sodium phosphate pH 8-9 as recommended by the manufacturer and filtered through a 0.22 μm filter. The conditioned medium were purified by affinity chromatography using a protein A column (GE) according to the manufacturer's instructions. The purified proteins were concentrated with a 50 kDa AMICON™ units (MILLIPORE) for IgG-ICK or 10 kDa for scFv-ICK. During this step, elution buffer was replaced by PBS. Proteins were finally assayed by ELISA and absorbance measuring at 280 nm. Purity was evaluated by electrophoresis.

Binding Activity of the Immunocytokines

The specific binding of the anti-HER2 IgG-ICK or scFv-ICK was assessed by flow cytometry on HER2 positive cells SK-BR-3 using anti-IL15 antibody. The capacity of ICK to bind IL-15 receptor on effector cells were tested on Kit225. ICK coated on targeted cells were revealed with a FITC-conjugated goat anti-murine IgG mAb (SIGMA-ALDRICH) or with a FITC-conjugated mouse anti-IL15 antibody (R&D SYSTEM). Targeted cells ($1\times10^5$) were incubated with each ICK for 1 h at 4° C., washed and then incubated with a FITC-conjugate for 1 h at 4° C. Washed cells were finally analyzed on a FACSCALIBUR™ (BECTON DICKINSON).

FIG. 3 shows flow cytometry evaluation of anti-HER2 (trastuzumab-IL15 and trastuzumab-122-IL15) on HER2 expressing SKBR3 cells.

FIG. 5 shows flow cytometry evaluation of the ICK Trastuzumab-RLI on HER2 expressing SKBR3 cells. Anti-HER2 ICK was compared on SKBR3 cells to the Trastuzumab (HERCEPTIN®, Genentech)

The results have shown the capacity of the ICK trastuzumab-RLI to coat tumor cell lines expressing the relevant TAA.

Proliferation Activity of the Immunocytokines

The interleukin-15 proliferation activity of the fusion of IL-15 and Trastuzumab or anti-HER2 scFv fragments was tested on Kit 225 and 32Dß cells by measuring [$^3$H]thymidine incorporation according to the method described previously.

Figure 11:
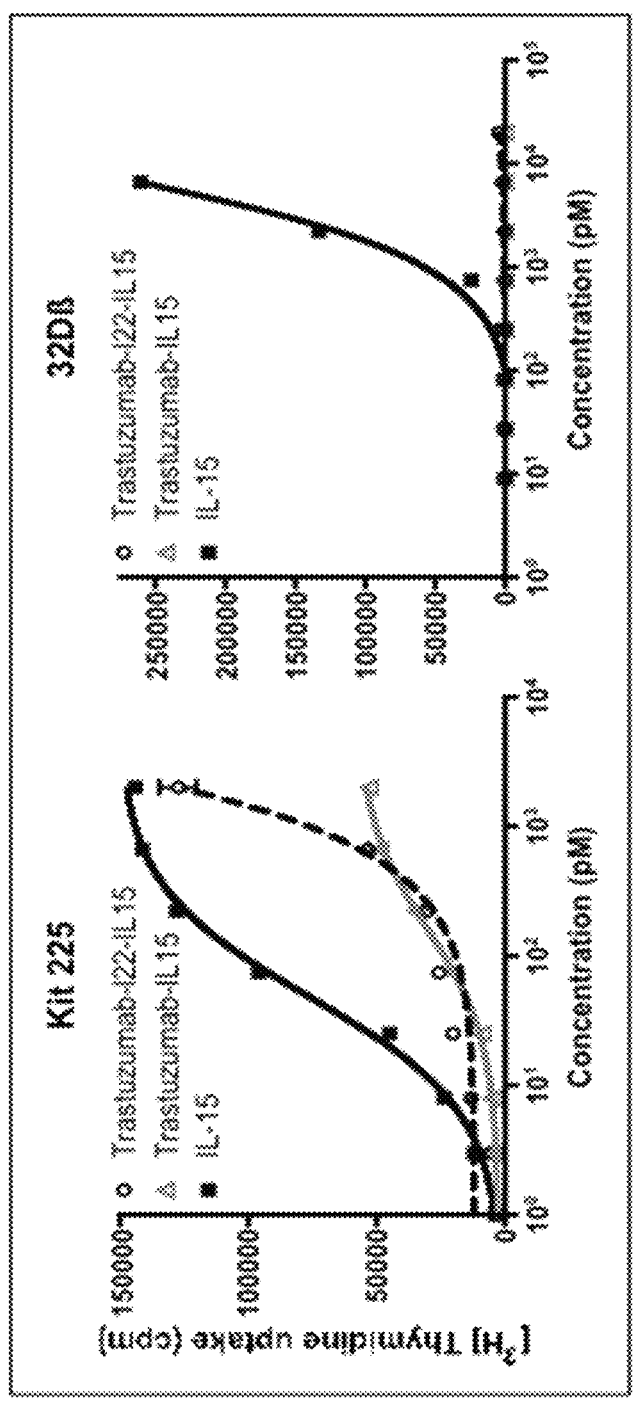
FIG. 11 show the activity of IL-15 anti-HER2 immunocytokines as compared to IL15.

The FIG. 11 shows [$^3$H]Thymidine incorporation by Kit 225 and 32Dß cells cultured with increasing concentrations of Trastuzumab-122-IL-15 (○), Trastuzumab-IL-15(Δ), and rIL-15 (■).

Figure 12:
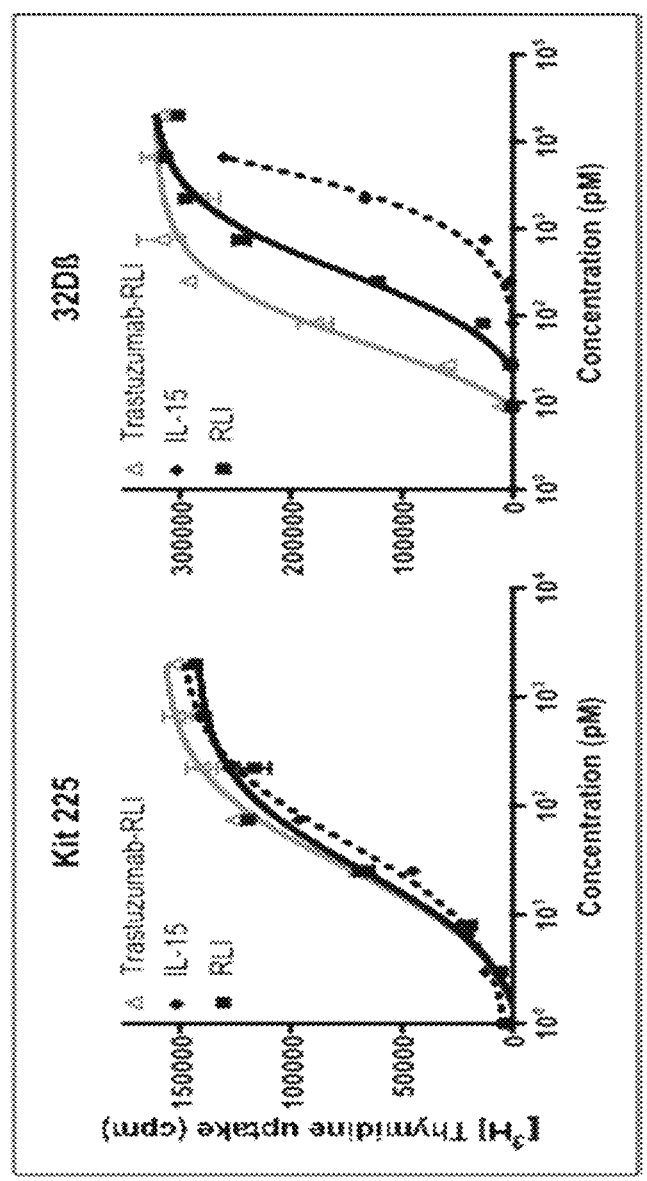
FIG. 12 shows the activity of RLI anti-HER2 immunocytokines as compared to IL15.

The FIG. 12 shows [$^3$H]Thymidine incorporation by Kit 225 and 32Dß cells cultured with increasing concentrations of Trastuzumab-RLI (Δ), RLI (■), and rIL-15 (◆).

The results show that the biological activity of IL-15 is drastically decreased on αβγ cells on the context of immunocytokine, meaning that conjugation of IL-15 with monoclonal antibody induces a loss of activity. Moreover, this loss is more important in absence of linker between the two moieties. On the βγ cells, conjugation completely abrogates the biological activity of IL-15 with or without linker.

In the context of RLI-derived immunocytokines despite IL15 immunocytokines, the results show that the biological activity of IL-15 is conserved meaning that conjugation of RLI with a monoclonal antibody permits surprisingly the conservation of this IL-15 activity. Moreover, this intriguing effect does not require any second linker between RLI and the monoclonal antibody.

Still surprisingly, the results show that the RLI-derived trastuzumab immunocytokines present a significant gain of biological activity as compared to free IL-15 in the βγ context (about 10 to 100 fold increase).

The results have further shown that, in the context of RLI-derived scFv immunocytokines despite IL15 immunocytokines, the biological activity of IL-15 is also conserved meaning that conjugation of RLI with a scFv fragment permits surprisingly the conservation of this IL-15 activity (data not shown). Again, this intriguing effect does not require any second linker between RLI and the scFv fragment (data not shown).

We claim:

1. An immunocytokine comprising:

a) a conjugate, and b) an antibody or a fragment thereof, wherein said fragment thereof is capable of reacting with the same antigen as its antibody counterpart, directly or indirectly linked by covalence to said conjugate, wherein said conjugate comprises:

(i) a polypeptide comprising the amino acid sequence of an interleukin 15, and (ii) a polypeptide comprising the amino acid sequence of a sushi domain of an interleukin-15 receptor alpha (IL-15Rα)

wherein the conjugate comprises the amino acid sequence of SEQ ID NO: 17.

2. The immunocytokine of claim 1, wherein the amino acid sequence of the conjugate and the amino acid sequence of the antibody or fragment thereof are not separated by any linker amino acid sequence.

3. The immunocytokine of claim 1, wherein the amino acid sequence of the conjugate and the amino acid sequence of the antibody or fragment thereof are separated by a linker amino acid sequence.

4. The immunocytokine of claim 1, wherein the antibody or fragment thereof is directed against an antigen selected from the group consisting of tumor neovascularization antigens and tumor extracellular matrix antigens.

5. The immunocytokine of claim 1, wherein the amino acid sequence of the conjugate is in a C-terminal position relative to the amino acid sequence of the antibody or fragment thereof.

6. The immunocytokine of claim 1, wherein the antibody or fragment thereof is directed against tumoral antigens.

7. A pharmaceutical composition comprising the immunocytokine as defined in claim 1, and a pharmaceutically acceptable carrier.

8. The pharmaceutical composition of claim 7, wherein said pharmaceutical composition is for treating cancer in a subject by an administration by injection at a dose of 2.5 mg/kg of subject or less.

* * * * *

SEQUENCE LISTING

```
<160> NUMBER OF SEQ ID NOS: 27

<210> SEQ ID NO 1
<211> LENGTH: 114
<212> TYPE: PRT
<213> ORGANISM: artificial sequence
<220> FEATURE:
<223> OTHER INFORMATION: mammalian interleukin 15 consensus sequence
<220> FEATURE:
<221> NAME/KEY: MISC_FEATURE
<222> LOCATION: (1)..(1)
<223> OTHER INFORMATION: X= N, S, T or I
<220> FEATURE:
<221> NAME/KEY: MISC_FEATURE
<222> LOCATION: (3)..(3)
<223> OTHER INFORMATION: X= V, H, I, Q or E
<220> FEATURE:
<221> NAME/KEY: MISC_FEATURE
<222> LOCATION: (4)..(4)
<223> OTHER INFORMATION: X= N, Y, F or D
<220> FEATURE:
<221> NAME/KEY: MISC_FEATURE
<222> LOCATION: (6)..(6)
<223> OTHER INFORMATION: X= I or R
<220> FEATURE:
<221> NAME/KEY: MISC_FEATURE
<222> LOCATION: (7)..(7)
<223> OTHER INFORMATION: X= S, N, L, Y, K or R
<220> FEATURE:
<221> NAME/KEY: MISC_FEATURE
<222> LOCATION: (10)..(10)
<223> OTHER INFORMATION: X= K, E, R or Q
<220> FEATURE:
```

```
<221> NAME/KEY: MISC_FEATURE
<222> LOCATION: (11)..(11)
<223> OTHER INFORMATION: X= K, T or R
<220> FEATURE:
<221> NAME/KEY: MISC_FEATURE
<222> LOCATION: (13)..(13)
<223> OTHER INFORMATION: X= E, D or Q
<220> FEATURE:
<221> NAME/KEY: MISC_FEATURE
<222> LOCATION: (14)..(14)
<223> OTHER INFORMATION: X= D, H, S or N
<220> FEATURE:
<221> NAME/KEY: MISC_FEATURE
<222> LOCATION: (16)..(16)
<223> OTHER INFORMATION: X= I or T
<220> FEATURE:
<221> NAME/KEY: MISC_FEATURE
<222> LOCATION: (17)..(17)
<223> OTHER INFORMATION: X=Q, R or K
<220> FEATURE:
<221> NAME/KEY: MISC_FEATURE
<222> LOCATION: (18)..(18)
<223> OTHER INFORMATION: X= S or F
<220> FEATURE:
<221> NAME/KEY: MISC_FEATURE
<222> LOCATION: (19)..(19)
<223> OTHER INFORMATION: X= M, I or L
<220> FEATURE:
<221> NAME/KEY: MISC_FEATURE
<222> LOCATION: (21)..(21)
<223> OTHER INFORMATION: X= I, V or M
<220> FEATURE:
<221> NAME/KEY: MISC_FEATURE
<222> LOCATION: (23)..(23)
<223> OTHER INFORMATION: X=A or T
<220> FEATURE:
<221> NAME/KEY: MISC_FEATURE
<222> LOCATION: (28)..(28)
<223> OTHER INFORMATION: X=E or D
<220> FEATURE:
<221> NAME/KEY: MISC_FEATURE
<222> LOCATION: (30)..(30)
<223> OTHER INFORMATION: X= D or G
<220> FEATURE:
<221> NAME/KEY: MISC_FEATURE
<222> LOCATION: (31)..(31)
<223> OTHER INFORMATION: X= V, F, A or I
<220> FEATURE:
<221> NAME/KEY: MISC_FEATURE
<222> LOCATION: (34)..(34)
<223> OTHER INFORMATION: X= S, N or R
<220> FEATURE:
<221> NAME/KEY: MISC_FEATURE
<222> LOCATION: (37)..(37)
<223> OTHER INFORMATION: X= V or I
<220> FEATURE:
<221> NAME/KEY: MISC_FEATURE
<222> LOCATION: (39)..(39)
<223> OTHER INFORMATION: X= A or T
<220> FEATURE:
<221> NAME/KEY: MISC_FEATURE
<222> LOCATION: (41)..(41)
<223> OTHER INFORMATION: X= K, Q or N
<220> FEATURE:
<221> NAME/KEY: MISC_FEATURE
<222> LOCATION: (48)..(48)
<223> OTHER INFORMATION: X= Q, G, R, H or E
<220> FEATURE:
<221> NAME/KEY: MISC_FEATURE
<222> LOCATION: (51)..(51)
<223> OTHER INFORMATION: X= S or L
<220> FEATURE:
<221> NAME/KEY: MISC_FEATURE
<222> LOCATION: (52)..(52)
<223> OTHER INFORMATION: X= L, Q or H
<220> FEATURE:
<221> NAME/KEY: MISC_FEATURE
<222> LOCATION: (54)..(54)
<223> OTHER INFORMATION: X= S, F or Y
```

-continued

```
<220> FEATURE:
<221> NAME/KEY: MISC_FEATURE
<222> LOCATION: (55)..(55)
<223> OTHER INFORMATION: X= G, K, S, N or R
<220> FEATURE:
<221> NAME/KEY: MISC_FEATURE
<222> LOCATION: (56)..(56)
<223> OTHER INFORMATION: X= D, H, S or N
<220> FEATURE:
<221> NAME/KEY: MISC_FEATURE
<222> LOCATION: (57)..(57)
<223> OTHER INFORMATION: X= A, H, M, E, G, S or T
<220> FEATURE:
<221> NAME/KEY: MISC_FEATURE
<222> LOCATION: (58)..(58)
<223> OTHER INFORMATION: X= S, V, P, T, N or D
<220> FEATURE:
<221> NAME/KEY: MISC_FEATURE
<222> LOCATION: (59)..(59)
<223> OTHER INFORMATION: X= I or L
<220> FEATURE:
<221> NAME/KEY: MISC_FEATURE
<222> LOCATION: (60)..(60)
<223> OTHER INFORMATION: X= H, S, K, N, Y or E
<220> FEATURE:
<221> NAME/KEY: MISC_FEATURE
<222> LOCATION: (61)..(61)
<223> OTHER INFORMATION: X= D or E
<220> FEATURE:
<221> NAME/KEY: MISC_FEATURE
<222> LOCATION: (62)..(62)
<223> OTHER INFORMATION: X= T, I or A
<220> FEATURE:
<221> NAME/KEY: MISC_FEATURE
<222> LOCATION: (63)..(63)
<223> OTHER INFORMATION: X= V or I
<220> FEATURE:
<221> NAME/KEY: MISC_FEATURE
<222> LOCATION: (64)..(64)
<223> OTHER INFORMATION: X= E, T, Q, R or K
<220> FEATURE:
<221> NAME/KEY: MISC_FEATURE
<222> LOCATION: (66)..(66)
<223> OTHER INFORMATION: X= L or V
<220> FEATURE:
<221> NAME/KEY: MISC_FEATURE
<222> LOCATION: (67)..(67)
<223> OTHER INFORMATION: X= I, T or L
<220> FEATURE:
<221> NAME/KEY: MISC_FEATURE
<222> LOCATION: (68)..(68)
<223> OTHER INFORMATION: X=I, M, F, Y or L
<220> FEATURE:
<221> NAME/KEY: MISC_FEATURE
<222> LOCATION: (72)..(72)
<223> OTHER INFORMATION: X= N, T, R, D or S
<220> FEATURE:
<221> NAME/KEY: MISC_FEATURE
<222> LOCATION: (73)..(73)
<223> OTHER INFORMATION: X= S, N, R, T or I
<220> FEATURE:
<221> NAME/KEY: MISC_FEATURE
<222> LOCATION: (75)..(75)
<223> OTHER INFORMATION: X= S or N
<220> FEATURE:
<221> NAME/KEY: MISC_FEATURE
<222> LOCATION: (76)..(76)
<223> OTHER INFORMATION: X= S or A
<220> FEATURE:
<221> NAME/KEY: MISC_FEATURE
<222> LOCATION: (77)..(77)
<223> OTHER INFORMATION: X= N, I or K
<220> FEATURE:
<221> NAME/KEY: MISC_FEATURE
<222> LOCATION: (78)..(78)
<223> OTHER INFORMATION: X= G, E or K
<220> FEATURE:
<221> NAME/KEY: MISC_FEATURE
<222> LOCATION: (79)..(79)
```

```
<223> OTHER INFORMATION: X= N, Y, D or T
<220> FEATURE:
<221> NAME/KEY: MISC_FEATURE
<222> LOCATION: (80)..(80)
<223> OTHER INFORMATION: X= V, K or I
<220> FEATURE:
<221> NAME/KEY: MISC_FEATURE
<222> LOCATION: (81)..(81)
<223> OTHER INFORMATION: X= T, A or I
<220> FEATURE:
<221> NAME/KEY: MISC_FEATURE
<222> LOCATION: (83)..(83)
<223> OTHER INFORMATION: X= S, L or T
<220> FEATURE:
<221> NAME/KEY: MISC_FEATURE
<222> LOCATION: (87)..(87)
<223> OTHER INFORMATION: X= E or V
<220> FEATURE:
<221> NAME/KEY: MISC_FEATURE
<222> LOCATION: (93)..(93)
<223> OTHER INFORMATION: X= E or K
<220> FEATURE:
<221> NAME/KEY: MISC_FEATURE
<222> LOCATION: (94)..(94)
<223> OTHER INFORMATION: X= K or R
<220> FEATURE:
<221> NAME/KEY: MISC_FEATURE
<222> LOCATION: (95)..(95)
<223> OTHER INFORMATION: X= N, T or S
<220> FEATURE:
<221> NAME/KEY: MISC_FEATURE
<222> LOCATION: (96)..(96)
<223> OTHER INFORMATION: X= I or F
<220> FEATURE:
<221> NAME/KEY: MISC_FEATURE
<222> LOCATION: (97)..(97)
<223> OTHER INFORMATION: X= K, N, A, or T
<220> FEATURE:
<221> NAME/KEY: MISC_FEATURE
<222> LOCATION: (101)..(101)
<223> OTHER INFORMATION: X= Q, K or E
<220> FEATURE:
<221> NAME/KEY: MISC_FEATURE
<222> LOCATION: (104)..(104)
<223> OTHER INFORMATION: X= V, I or K
<220> FEATURE:
<221> NAME/KEY: MISC_FEATURE
<222> LOCATION: (105)..(105)
<223> OTHER INFORMATION: X= H or R
<220> FEATURE:
<221> NAME/KEY: MISC_FEATURE
<222> LOCATION: (112)..(112)
<223> OTHER INFORMATION: X= N or Y
<220> FEATURE:
<221> NAME/KEY: MISC_FEATURE
<222> LOCATION: (113)..(113)
<223> OTHER INFORMATION: X= = T, S, P, L or A
<220> FEATURE:
<221> NAME/KEY: MISC_FEATURE
<222> LOCATION: (114)..(114)
<223> OTHER INFORMATION: X= = S or P

<400> SEQUENCE: 1

Xaa Trp Xaa Xaa Val Xaa Xaa Asp Leu Xaa Xaa Ile Xaa Xaa Leu Xaa
1               5                   10                  15

Xaa Xaa Xaa His Xaa Asp Xaa Thr Leu Tyr Thr Xaa Ser Xaa Xaa His
            20                  25                  30

Pro Xaa Cys Lys Xaa Thr Xaa Met Xaa Cys Phe Leu Leu Glu Leu Xaa
        35                  40                  45

Val Ile Xaa Xaa Glu Xaa Xaa Xaa Xaa Xaa Xaa Xaa Xaa Xaa Xaa Xaa
    50                  55                  60

Asn Xaa Xaa Xaa Leu Ala Asn Xaa Xaa Leu Xaa Xaa Xaa Xaa Xaa Xaa
65                  70                  75                  80
```

-continued

Xaa Glu Xaa Gly Cys Lys Xaa Cys Glu Glu Leu Glu Xaa Xaa Xaa Xaa
            85                  90                  95

Xaa Glu Phe Leu Xaa Ser Phe Xaa Xaa Ile Val Gln Met Phe Ile Xaa
            100                 105                 110

Xaa Xaa

<210> SEQ ID NO 2
<211> LENGTH: 114
<212> TYPE: PRT
<213> ORGANISM: Artificial Sequence
<220> FEATURE:
<223> OTHER INFORMATION: primate uinterleukin 15 consensus sequence
<220> FEATURE:
<221> NAME/KEY: MISC_FEATURE
<222> LOCATION: (1)..(1)
<223> OTHER INFORMATION: X = N or I
<220> FEATURE:
<221> NAME/KEY: MISC_FEATURE
<222> LOCATION: (4)..(4)
<223> OTHER INFORMATION: X = N or D
<220> FEATURE:
<221> NAME/KEY: MISC_FEATURE
<222> LOCATION: (10)..(10)
<223> OTHER INFORMATION: X = K or R
<220> FEATURE:
<221> NAME/KEY: MISC_FEATURE
<222> LOCATION: (11)..(11)
<223> OTHER INFORMATION: X = K or R
<220> FEATURE:
<221> NAME/KEY: MISC_FEATURE
<222> LOCATION: (13)..(13)
<223> OTHER INFORMATION: X = E or Q
<220> FEATURE:
<221> NAME/KEY: MISC_FEATURE
<222> LOCATION: (16)..(16)
<223> OTHER INFORMATION: X = I or T
<220> FEATURE:
<221> NAME/KEY: MISC_FEATURE
<222> LOCATION: (19)..(19)
<223> OTHER INFORMATION: X = M or I
<220> FEATURE:
<221> NAME/KEY: MISC_FEATURE
<222> LOCATION: (30)..(30)
<223> OTHER INFORMATION: X = D or G
<220> FEATURE:
<221> NAME/KEY: MISC_FEATURE
<222> LOCATION: (31)..(31)
<223> OTHER INFORMATION: X = V or I
<220> FEATURE:
<221> NAME/KEY: MISC_FEATURE
<222> LOCATION: (34)..(34)
<223> OTHER INFORMATION: X = S or R
<220> FEATURE:
<221> NAME/KEY: MISC_FEATURE
<222> LOCATION: (52)..(52)
<223> OTHER INFORMATION: X = L or H
<220> FEATURE:
<221> NAME/KEY: MISC_FEATURE
<222> LOCATION: (55)..(55)
<223> OTHER INFORMATION: X = G or N
<220> FEATURE:
<221> NAME/KEY: MISC_FEATURE
<222> LOCATION: (56)..(56)
<223> OTHER INFORMATION: X = D or N
<220> FEATURE:
<221> NAME/KEY: MISC_FEATURE
<222> LOCATION: (57)..(57)
<223> OTHER INFORMATION: X = A or T
<220> FEATURE:
<221> NAME/KEY: MISC_FEATURE
<222> LOCATION: (58)..(58)
<223> OTHER INFORMATION: X = S, N or D
<220> FEATURE:
<221> NAME/KEY: MISC_FEATURE
<222> LOCATION: (60)..(60)
<223> OTHER INFORMATION: X = H or N

```
<220> FEATURE:
<221> NAME/KEY: MISC_FEATURE
<222> LOCATION: (63)..(63)
<223> OTHER INFORMATION: X = V or I
<220> FEATURE:
<221> NAME/KEY: MISC_FEATURE
<222> LOCATION: (67)..(67)
<223> OTHER INFORMATION: X = I or L
<220> FEATURE:
<221> NAME/KEY: MISC_FEATURE
<222> LOCATION: (72)..(72)
<223> OTHER INFORMATION: X = N or R
<220> FEATURE:
<221> NAME/KEY: MISC_FEATURE
<222> LOCATION: (73)..(73)
<223> OTHER INFORMATION: X =S or I
<220> FEATURE:
<221> NAME/KEY: MISC_FEATURE
<222> LOCATION: (76)..(76)
<223> OTHER INFORMATION: X =S or A
<220> FEATURE:
<221> NAME/KEY: MISC_FEATURE
<222> LOCATION: (79)..(79)
<223> OTHER INFORMATION: X =N or T
<220> FEATURE:
<221> NAME/KEY: MISC_FEATURE
<222> LOCATION: (80)..(80)
<223> OTHER INFORMATION: X =V or I
<220> FEATURE:
<221> NAME/KEY: MISC_FEATURE
<222> LOCATION: (93)..(93)
<223> OTHER INFORMATION: X =E or K
<220> FEATURE:
<221> NAME/KEY: MISC_FEATURE
<222> LOCATION: (112)..(112)
<223> OTHER INFORMATION: X = N or Y
<220> FEATURE:
<221> NAME/KEY: MISC_FEATURE
<222> LOCATION: (113)..(113)
<223> OTHER INFORMATION: X = T or A

<400> SEQUENCE: 2

Xaa Trp Val Xaa Val Ile Ser Asp Leu Xaa Xaa Ile Xaa Asp Leu Xaa
1               5                   10                  15

Gln Ser Xaa His Ile Asp Ala Thr Leu Tyr Thr Glu Ser Xaa Xaa His
            20                  25                  30

Pro Xaa Cys Lys Val Thr Ala Met Lys Cys Phe Leu Leu Glu Leu Gln
        35                  40                  45

Val Ile Ser Xaa Glu Ser Xaa Xaa Xaa Xaa Ile Xaa Asp Thr Xaa Glu
50                  55                  60

Asn Leu Xaa Ile Leu Ala Asn Xaa Xaa Leu Ser Xaa Asn Gly Xaa Xaa
65                  70                  75                  80

Thr Glu Ser Gly Cys Lys Glu Cys Glu Glu Leu Glu Xaa Lys Asn Ile
                85                  90                  95

Lys Glu Phe Leu Gln Ser Phe Val His Ile Val Gln Met Phe Ile Xaa
            100                 105                 110

Xaa Ser

<210> SEQ ID NO 3
<211> LENGTH: 114
<212> TYPE: PRT
<213> ORGANISM: Homo sapiens
<220> FEATURE:
<221> NAME/KEY: VARIANT
<222> LOCATION: (93)..(93)
<223> OTHER INFORMATION: X= E or K

<400> SEQUENCE: 3

Asn Trp Val Asn Val Ile Ser Asp Leu Lys Lys Ile Glu Asp Leu Ile
```

-continued

```
                1               5                   10                  15
            Gln Ser Met His Ile Asp Ala Thr Leu Tyr Thr Glu Ser Asp Val His
                            20                  25                  30
            Pro Ser Cys Lys Val Thr Ala Met Lys Cys Phe Leu Leu Glu Leu Gln
                                35                  40                  45
            Val Ile Ser Leu Glu Ser Gly Asp Ala Ser Ile His Asp Thr Val Glu
                    50                  55                  60
            Asn Leu Ile Ile Leu Ala Asn Asn Ser Leu Ser Ser Asn Gly Asn Val
             65                  70                  75                  80
            Thr Glu Ser Gly Cys Lys Glu Cys Glu Glu Leu Glu Xaa Lys Asn Ile
                            85                  90                  95
            Lys Glu Phe Leu Gln Ser Phe Val His Ile Val Gln Met Phe Ile Asn
                                100                 105                 110
            Thr Ser

<210> SEQ ID NO 4
<211> LENGTH: 61
<212> TYPE: PRT
<213> ORGANISM: Artificial Sequence
<220> FEATURE:
<223> OTHER INFORMATION: mammalian sushi domain consensus sequence
<220> FEATURE:
<221> NAME/KEY: MISC_FEATURE
<222> LOCATION: (3)..(3)
<223> OTHER INFORMATION: X= P or A
<220> FEATURE:
<221> NAME/KEY: MISC_FEATURE
<222> LOCATION: (5)..(5)
<223> OTHER INFORMATION: X= M or V
<220> FEATURE:
<221> NAME/KEY: MISC_FEATURE
<222> LOCATION: (7)..(7)
<223> OTHER INFORMATION: X= V or I
<220> FEATURE:
<221> NAME/KEY: MISC_FEATURE
<222> LOCATION: (13)..(13)
<223> OTHER INFORMATION: X= W, R or Q
<220> FEATURE:
<221> NAME/KEY: MISC_FEATURE
<222> LOCATION: (16)..(16)
<223> OTHER INFORMATION: X= S or N
<220> FEATURE:
<221> NAME/KEY: MISC_FEATURE
<222> LOCATION: (19)..(19)
<223> OTHER INFORMATION: X= L or V
<220> FEATURE:
<221> NAME/KEY: MISC_FEATURE
<222> LOCATION: (20)..(20)
<223> OTHER INFORMATION: X= Y, H or N
<220> FEATURE:
<221> NAME/KEY: MISC_FEATURE
<222> LOCATION: (26)..(26)
<223> OTHER INFORMATION: X= I or V
<220> FEATURE:
<221> NAME/KEY: MISC_FEATURE
<222> LOCATION: (39)..(39)
<223> OTHER INFORMATION: X= S or T
<220> FEATURE:
<221> NAME/KEY: MISC_FEATURE
<222> LOCATION: (41)..(41)
<223> OTHER INFORMATION: X=T or I
<220> FEATURE:
<221> NAME/KEY: MISC_FEATURE
<222> LOCATION: (45)..(45)
<223> OTHER INFORMATION: X=T or I
<220> FEATURE:
<221> NAME/KEY: MISC_FEATURE
<222> LOCATION: (45)..(45)
<223> OTHER INFORMATION: X= L or I
<220> FEATURE:
<221> NAME/KEY: MISC_FEATURE
```

-continued

```
<222> LOCATION: (48)..(48)
<223> OTHER INFORMATION: X= A or N
<220> FEATURE:
<221> NAME/KEY: MISC_FEATURE
<222> LOCATION: (51)..(51)
<223> OTHER INFORMATION: X= V or A
<220> FEATURE:
<221> NAME/KEY: MISC_FEATURE
<222> LOCATION: (53)..(53)
<223> OTHER INFORMATION: X= H or Y

<400> SEQUENCE: 4

Cys Pro Xaa Pro Xaa Ser Xaa Glu His Ala Asp Ile Xaa Val Lys Xaa
1               5                   10                  15

Tyr Ser Xaa Xaa Ser Arg Glu Arg Tyr Xaa Cys Asn Ser Gly Phe Lys
            20                  25                  30

Arg Lys Ala Gly Thr Ser Xaa Leu Xaa Glu Cys Val Xaa Asn Lys Xaa
                35                  40                  45

Thr Asn Xaa Ala Xaa Trp Thr Thr Pro Ser Leu Lys Cys
            50                  55                  60

<210> SEQ ID NO 5
<211> LENGTH: 64
<212> TYPE: PRT
<213> ORGANISM: Artificial Sequence
<220> FEATURE:
<223> OTHER INFORMATION: enlarged mammalian sushi domain consensus
      sequence
<220> FEATURE:
<221> NAME/KEY: MISC_FEATURE
<222> LOCATION: (1)..(1)
<223> OTHER INFORMATION: X= T, V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (9)..(9)
<223> OTHER INFORMATION: X= V or I
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (18)..(18)
<223> OTHER INFORMATION: X= S or N
<220> FEATURE:
<221> NAME/KEY: MISC_FEATURE
<222> LOCATION: (21)..(21)
<223> OTHER INFORMATION: X=L or V
<220> FEATURE:
<221> NAME/KEY: MISC_FEATURE
<222> LOCATION: (22)..(22)
<223> OTHER INFORMATION: X=Y, H or N
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (41)..(41)
<223> OTHER INFORMATION: X= S or T
<220> FEATURE:
<221> NAME/KEY: MISC_FEATURE
<222> LOCATION: (43)..(43)
<223> OTHER INFORMATION: X= T or I
<220> FEATURE:
<221> NAME/KEY: MISC_FEATURE
```

```
<222> LOCATION: (47)..(47)
<223> OTHER INFORMATION: X= L or I
<220> FEATURE:
<221> NAME/KEY: MISC_FEATURE
<222> LOCATION: (50)..(50)
<223> OTHER INFORMATION: X= A or N
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y

<400> SEQUENCE: 5

Xaa Thr Cys Pro Xaa Pro Xaa Ser Xaa Glu His Ala Asp Ile Xaa Val
1               5                   10                  15

Lys Xaa Tyr Ser Xaa Xaa Ser Arg Glu Arg Tyr Xaa Cys Asn Ser Gly
            20                  25                  30

Phe Lys Arg Lys Ala Gly Thr Ser Xaa Leu Xaa Glu Cys Val Xaa Asn
        35                  40                  45

Lys Xaa Thr Asn Xaa Ala Xaa Trp Thr Thr Pro Ser Leu Lys Cys Ile
50                  55                  60

<210> SEQ ID NO 6
<211> LENGTH: 61
<212> TYPE: PRT
<213> ORGANISM: Artificial Sequence
<220> FEATURE:
<223> OTHER INFORMATION: primate sushi domain consensus sequence
<220> FEATURE:
<221> NAME/KEY: MISC_FEATURE
<222> LOCATION: (3)..(3)
<223> OTHER INFORMATION: X= P or A
<220> FEATURE:
<221> NAME/KEY: MISC_FEATURE
<222> LOCATION: (5)..(5)
<223> OTHER INFORMATION: X= M or V
<220> FEATURE:
<221> NAME/KEY: MISC_FEATURE
<222> LOCATION: (13)..(13)
<223> OTHER INFORMATION: X= W, R or Q
<220> FEATURE:
<221> NAME/KEY: MISC_FEATURE
<222> LOCATION: (20)..(20)
<223> OTHER INFORMATION: X= Y or H
<220> FEATURE:
<221> NAME/KEY: MISC_FEATURE
<222> LOCATION: (26)..(26)
<223> OTHER INFORMATION: X= I or V
<220> FEATURE:
<221> NAME/KEY: MISC_FEATURE
<222> LOCATION: (51)..(51)
<223> OTHER INFORMATION: X= V or A
<220> FEATURE:
<221> NAME/KEY: MISC_FEATURE
<222> LOCATION: (53)..(53)
<223> OTHER INFORMATION: X= V or A

<400> SEQUENCE: 6

Cys Pro Xaa Pro Xaa Ser Val Glu His Ala Asp Ile Xaa Val Lys Ser
1               5                   10                  15

Tyr Ser Leu Xaa Ser Arg Glu Arg Tyr Xaa Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Xaa Ala Xaa Trp Thr Thr Pro Ser Leu Lys Cys
50                  55                  60
```

```
<210> SEQ ID NO 7
<211> LENGTH: 63
<212> TYPE: PRT
<213> ORGANISM: Artificial Sequence
<220> FEATURE:
<223> OTHER INFORMATION: enlarged primate sushi domain consensus
      sequence
<220> FEATURE:
<221> NAME/KEY: MISC_FEATURE
<222> LOCATION: (1)..(1)
<223> OTHER INFORMATION: X= V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (22)..(22)
<223> OTHER INFORMATION: X= Y or H
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (53)..(53)
<223> OTHER INFORMATION: X=V or A
<220> FEATURE:
<221> NAME/KEY: MISC_FEATURE
<222> LOCATION: (55)..(55)
<223> OTHER INFORMATION: X=H or Y

<400> SEQUENCE: 7

Xaa Thr Cys Pro Xaa Pro Xaa Ser Val Glu His Ala Asp Ile Xaa Val
1               5                   10                  15

Lys Ser Tyr Ser Leu Xaa Ser Arg Glu Arg Tyr Xaa Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Xaa Ala Xaa Trp Thr Thr Pro Ser Leu Lys Cys
    50                  55                  60

<210> SEQ ID NO 8
<211> LENGTH: 61
<212> TYPE: PRT
<213> ORGANISM: Homo sapiens

<400> SEQUENCE: 8

Cys Pro Pro Pro Met Ser Val Glu His Ala Asp Ile Trp Val Lys Ser
1               5                   10                  15

Tyr Ser Leu Tyr Ser Arg Glu Arg Tyr Ile Cys Asn Ser Gly Phe Lys
            20                  25                  30

Arg Lys Ala Gly Thr Ser Ser Leu Thr Glu Cys Val Leu Asn Lys Ala
        35                  40                  45

Thr Asn Val Ala His Trp Thr Thr Pro Ser Leu Lys Cys
    50                  55                  60

<210> SEQ ID NO 9
<211> LENGTH: 64
<212> TYPE: PRT
```

<213> ORGANISM: Homo sapiens

<400> SEQUENCE: 9

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60
```

<210> SEQ ID NO 10
<211> LENGTH: 77
<212> TYPE: PRT
<213> ORGANISM: Artificial Sequence
<220> FEATURE:
<223> OTHER INFORMATION: mammalian sushi and domains consensus sequence
<220> FEATURE:
<221> NAME/KEY: MISC_FEATURE
<222> LOCATION: (1)..(1)
<223> OTHER INFORMATION: X= T, V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
<222> LOCATION: (9)..(9)
<223> OTHER INFORMATION: X= V or I
<220> FEATURE:
<221> NAME/KEY: MISC_FEATURE
<222> LOCATION: (15)..(15)
<223> OTHER INFORMATION: X= W, R or Q
<220> FEATURE:
<221> NAME/KEY: MISC_FEATURE
<222> LOCATION: (18)..(18)
<223> OTHER INFORMATION: X= S or N
<220> FEATURE:
<221> NAME/KEY: MISC_FEATURE
<222> LOCATION: (21)..(21)
<223> OTHER INFORMATION: X= L or V
<220> FEATURE:
<221> NAME/KEY: MISC_FEATURE
<222> LOCATION: (22)..(22)
<223> OTHER INFORMATION: X= Y, H or N
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (41)..(41)
<223> OTHER INFORMATION: X= S or T
<220> FEATURE:
<221> NAME/KEY: MISC_FEATURE
<222> LOCATION: (43)..(43)
<223> OTHER INFORMATION: X= T or I
<220> FEATURE:
<221> NAME/KEY: MISC_FEATURE
<222> LOCATION: (47)..(47)
<223> OTHER INFORMATION: X= L or I
<220> FEATURE:
<221> NAME/KEY: MISC_FEATURE
<222> LOCATION: (50)..(50)
<223> OTHER INFORMATION: X=A or N
<220> FEATURE:
<221> NAME/KEY: MISC_FEATURE
<222> LOCATION: (53)..(53)
<223> OTHER INFORMATION: X= V or A

```
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (68)..(68)
<223> OTHER INFORMATION: X=A, S or L
<220> FEATURE:
<221> NAME/KEY: MISC_FEATURE
<222> LOCATION: (70)..(70)
<223> OTHER INFORMATION: X= V, A, S or T
<220> FEATURE:
<221> NAME/KEY: MISC_FEATURE
<222> LOCATION: (71)..(71)
<223> OTHER INFORMATION: X= H or R
<220> FEATURE:
<221> NAME/KEY: MISC_FEATURE
<222> LOCATION: (72)..(72)
<223> OTHER INFORMATION: X= Q or H
<220> FEATURE:
<221> NAME/KEY: MISC_FEATURE
<222> LOCATION: (73)..(73)
<223> OTHER INFORMATION: X= R, S or K
<220> FEATURE:
<221> NAME/KEY: MISC_FEATURE
<222> LOCATION: (75)..(75)
<223> OTHER INFORMATION: X= A, V or P
<220> FEATURE:
<221> NAME/KEY: MISC_FEATURE
<222> LOCATION: (76)..(76)
<223> OTHER INFORMATION: X= P or S
<220> FEATURE:
<221> NAME/KEY: MISC_FEATURE
<222> LOCATION: (77)..(77)
<223> OTHER INFORMATION: X= P or T

<400> SEQUENCE: 10

Xaa Thr Cys Pro Xaa Pro Xaa Ser Xaa Glu His Ala Asp Ile Xaa Val
1               5                   10                  15

Lys Xaa Tyr Ser Xaa Xaa Ser Arg Glu Arg Tyr Xaa Cys Asn Ser Gly
            20                  25                  30

Phe Lys Arg Lys Ala Gly Thr Ser Xaa Leu Xaa Glu Cys Val Xaa Asn
        35                  40                  45

Lys Xaa Thr Asn Xaa Ala Xaa Trp Thr Thr Pro Ser Leu Lys Cys Ile
    50                  55                  60

Arg Asp Pro Xaa Leu Xaa Xaa Xaa Xaa Pro Xaa Xaa Xaa
65                  70                  75

<210> SEQ ID NO 11
<211> LENGTH: 77
<212> TYPE: PRT
<213> ORGANISM: Artificial Sequence
<220> FEATURE:
<223> OTHER INFORMATION: primate sushi and domains consensus sequence
<220> FEATURE:
<221> NAME/KEY: MISC_FEATURE
<222> LOCATION: (1)..(1)
<223> OTHER INFORMATION: X= V or I
<220> FEATURE:
<221> NAME/KEY: MISC_FEATURE
<222> LOCATION: (5)..(5)
<223> OTHER INFORMATION: X= P or A
<220> FEATURE:
<221> NAME/KEY: MISC_FEATURE
<222> LOCATION: (7)..(7)
<223> OTHER INFORMATION: X= M or V
<220> FEATURE:
<221> NAME/KEY: MISC_FEATURE
```

```
<222> LOCATION: (15)..(15)
<223> OTHER INFORMATION: X= W, R or Q
<220> FEATURE:
<221> NAME/KEY: MISC_FEATURE
<222> LOCATION: (22)..(22)
<223> OTHER INFORMATION: X= Y or H
<220> FEATURE:
<221> NAME/KEY: MISC_FEATURE
<222> LOCATION: (28)..(28)
<223> OTHER INFORMATION: X= I or V
<220> FEATURE:
<221> NAME/KEY: MISC_FEATURE
<222> LOCATION: (53)..(53)
<223> OTHER INFORMATION: X= V or A
<220> FEATURE:
<221> NAME/KEY: MISC_FEATURE
<222> LOCATION: (55)..(55)
<223> OTHER INFORMATION: X= H or Y
<220> FEATURE:
<221> NAME/KEY: MISC_FEATURE
<222> LOCATION: (68)..(68)
<223> OTHER INFORMATION: X= A, S or L
<220> FEATURE:
<221> NAME/KEY: MISC_FEATURE
<222> LOCATION: (70)..(70)
<223> OTHER INFORMATION: X= V, A or T
<220> FEATURE:
<221> NAME/KEY: MISC_FEATURE
<222> LOCATION: (71)..(71)
<223> OTHER INFORMATION: X= H or R
<220> FEATURE:
<221> NAME/KEY: MISC_FEATURE
<222> LOCATION: (75)..(75)
<223> OTHER INFORMATION: X= A or V

<400> SEQUENCE: 11

Xaa Thr Cys Pro Xaa Pro Xaa Ser Val Glu His Ala Asp Ile Xaa Val
1               5                   10                  15

Lys Ser Tyr Ser Leu Xaa Ser Arg Glu Arg Tyr Xaa Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Xaa Ala Xaa Trp Thr Thr Pro Ser Leu Lys Cys Ile
    50                  55                  60

Arg Asp Pro Xaa Leu Xaa Xaa Gln Arg Pro Xaa Pro Pro
65                  70                  75

<210> SEQ ID NO 12
<211> LENGTH: 77
<212> TYPE: PRT
<213> ORGANISM: Homo sapiens

<400> SEQUENCE: 12

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro
65                  70                  75

<210> SEQ ID NO 13
<211> LENGTH: 20
<212> TYPE: PRT
```

-continued

```
<213> ORGANISM: Artificial Sequence
<220> FEATURE:
<223> OTHER INFORMATION: peptidic linker

<400> SEQUENCE: 13

Ser Gly Gly Ser Gly Gly Gly Gly Ser Gly Gly Gly Ser Gly Gly
1               5                   10                  15

Gly Ser Leu Gln
            20

<210> SEQ ID NO 14
<211> LENGTH: 20
<212> TYPE: PRT
<213> ORGANISM: Artificial Sequence
<220> FEATURE:
<223> OTHER INFORMATION: peptidic linker

<400> SEQUENCE: 14

Ser Gly Gly Ser Gly Gly Gly Gly Ser Gly Gly Gly Ser Gly Gly
1               5                   10                  15

Gly Ser Gly Gly
            20

<210> SEQ ID NO 15
<211> LENGTH: 21
<212> TYPE: PRT
<213> ORGANISM: Artificial Sequence
<220> FEATURE:
<223> OTHER INFORMATION: peptidic linker

<400> SEQUENCE: 15

Ser Gly Gly Gly Ser Gly Gly Gly Gly Ser Gly Gly Gly Ser Gly
1               5                   10                  15

Gly Gly Ser Leu Gln
            20

<210> SEQ ID NO 16
<211> LENGTH: 22
<212> TYPE: PRT
<213> ORGANISM: Artificial Sequence
<220> FEATURE:
<223> OTHER INFORMATION: peptidic linker

<400> SEQUENCE: 16

Ser Gly Gly Gly Gly Ser Gly Gly Gly Gly Ser Gly Gly Gly Ser
1               5                   10                  15

Gly Gly Gly Gly Ser Gly
            20

<210> SEQ ID NO 17
<211> LENGTH: 211
<212> TYPE: PRT
<213> ORGANISM: Artificial Sequence
<220> FEATURE:
<223> OTHER INFORMATION: RLI

<400> SEQUENCE: 17

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45
```

Lys Ala Thr Asn Val Ala His Trp Thr Thr Pro Ser Leu Lys Cys Ile
        50                  55                  60

Arg Asp Pro Ala Leu Val His Gln Arg Pro Ala Pro Pro Ser Gly Gly
65                  70                  75                  80

Ser Gly Gly Gly Gly Ser Gly Gly Ser Gly Gly Gly Gly Ser Gly
                85                  90                  95

Gly Asn Trp Val Asn Val Ile Ser Asp Leu Lys Lys Ile Glu Asp Leu
                100                 105                 110

Ile Gln Ser Met His Ile Asp Ala Thr Leu Tyr Thr Glu Ser Asp Val
                115                 120                 125

His Pro Ser Cys Lys Val Thr Ala Met Lys Cys Phe Leu Leu Glu Leu
        130                 135                 140

Gln Val Ile Ser Leu Glu Ser Gly Asp Ala Ser Ile His Asp Thr Val
145                 150                 155                 160

Glu Asn Leu Ile Ile Leu Ala Asn Asn Ser Leu Ser Ser Asn Gly Asn
                165                 170                 175

Val Thr Glu Ser Gly Cys Lys Glu Cys Glu Glu Leu Glu Glu Lys Asn
                180                 185                 190

Ile Lys Glu Phe Leu Gln Ser Phe Val His Ile Val Gln Met Phe Ile
                195                 200                 205

Asn Thr Ser
210

<210> SEQ ID NO 18
<211> LENGTH: 234
<212> TYPE: PRT
<213> ORGANISM: Artificial Sequence
<220> FEATURE:
<223> OTHER INFORMATION: ANti-HER2Neu light chain

<400> SEQUENCE: 18

Met Ala Arg Ser Val Thr Leu Val Phe Leu Val Leu Val Ser Leu Thr
1               5                   10                  15

Gly Leu Tyr Ala Asp Ile Val Met Thr Gln Ser His Lys Phe Met Ser
                20                  25                  30

Thr Ser Val Gly Asp Arg Val Ser Ile Thr Cys Lys Ala Ser Gln Asp
                35                  40                  45

Val Asn Thr Ala Val Ala Trp Tyr Gln Gln Lys Pro Gly His Ser Pro
        50                  55                  60

Lys Leu Leu Ile Tyr Ser Ala Ser Phe Arg Tyr Thr Gly Val Pro Asp
65                  70                  75                  80

Arg Phe Thr Gly Asn Arg Ser Gly Thr Asp Phe Thr Phe Thr Ile Ser
                85                  90                  95

Ser Val Gln Ala Glu Asp Leu Ala Val Tyr Tyr Cys Gln Gln His Tyr
                100                 105                 110

Thr Thr Pro Pro Thr Phe Gly Gly Gly Thr Lys Val Glu Ile Lys Arg
                115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

```
Tyr Ser Met Ser Ser Thr Leu Thr Leu Thr Lys Asp Glu Tyr Glu Arg
            195                 200                 205
His Asn Ser Tyr Thr Cys Glu Ala Thr His Lys Thr Ser Thr Ser Pro
        210                 215                 220
Ile Val Lys Ser Phe Asn Arg Asn Glu Cys
225                 230
```

```
<210> SEQ ID NO 19
<211> LENGTH: 464
<212> TYPE: PRT
<213> ORGANISM: Artificial Sequence
<220> FEATURE:
<223> OTHER INFORMATION: Anti-HER2Neu heavy chain

<400> SEQUENCE: 19
```

```
Met Ala Arg Ser Val Thr Leu Val Phe Leu Val Leu Val Ser Leu Thr
1               5                   10                  15
Gly Leu Tyr Ala Gln Val Gln Leu Gln Gln Ser Gly Pro Glu Leu Val
            20                  25                  30
Lys Pro Gly Ala Ser Leu Lys Leu Ser Cys Thr Ala Ser Gly Phe Asn
        35                  40                  45
Ile Lys Asp Thr Tyr Ile His Trp Val Lys Gln Arg Pro Glu Gln Gly
    50                  55                  60
Leu Glu Trp Ile Gly Arg Ile Tyr Pro Thr Asn Gly Tyr Thr Arg Tyr
65                  70                  75                  80
Asp Pro Lys Phe Gln Asp Lys Ala Thr Ile Thr Ala Asp Thr Ser Ser
                85                  90                  95
Asn Thr Ala Tyr Leu Gln Val Ser Arg Leu Thr Ser Glu Asp Thr Ala
            100                 105                 110
Val Tyr Tyr Cys Ser Arg Trp Gly Gly Asp Gly Phe Tyr Ala Met Asp
        115                 120                 125
Tyr Trp Gly Gln Gly Ala Ser Val Thr Val Ser Ser Ala Lys Thr Thr
    130                 135                 140
Pro Pro Ser Val Tyr Pro Leu Ala Pro Gly Ser Ala Ala Gln Thr Asn
145                 150                 155                 160
Ser Met Val Thr Leu Gly Cys Leu Val Lys Gly Tyr Phe Pro Glu Pro
                165                 170                 175
Val Thr Val Thr Trp Asn Ser Gly Ser Leu Ser Ser Gly Val His Thr
            180                 185                 190
Phe Pro Ala Val Leu Gln Ser Asp Leu Tyr Thr Leu Ser Ser Ser Val
        195                 200                 205
Thr Val Pro Ser Ser Thr Trp Pro Ser Glu Thr Val Thr Cys Asn Val
    210                 215                 220
Ala His Pro Ala Ser Ser Thr Lys Val Asp Lys Lys Ile Val Pro Arg
225                 230                 235                 240
Asp Cys Gly Cys Lys Pro Cys Ile Cys Thr Val Pro Glu Val Ser Ser
                245                 250                 255
Val Phe Ile Phe Pro Pro Lys Pro Lys Asp Val Leu Thr Ile Thr Leu
            260                 265                 270
Thr Pro Lys Val Thr Cys Val Val Asp Ile Ser Lys Asp Asp Pro
        275                 280                 285
Glu Val Gln Phe Ser Trp Phe Val Asp Asp Val Glu Val His Thr Ala
    290                 295                 300
Gln Thr Gln Pro Arg Glu Glu Gln Phe Asn Ser Thr Phe Arg Ser Val
305                 310                 315                 320
```

```
Ser Glu Leu Pro Ile Met His Gln Asp Trp Leu Asn Gly Lys Glu Phe
            325                 330                 335

Lys Cys Arg Val Asn Ser Ala Ala Phe Pro Ala Pro Ile Glu Lys Thr
        340                 345                 350

Ile Ser Lys Thr Lys Gly Arg Pro Lys Ala Pro Gln Val Tyr Thr Ile
            355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460
```

<210> SEQ ID NO 20
<211> LENGTH: 600
<212> TYPE: PRT
<213> ORGANISM: Artificial Sequence
<220> FEATURE:
<223> OTHER INFORMATION: IL15-L22-anti HER2Neu heavy chain

<400> SEQUENCE: 20

```
Met Ala Arg Ser Val Thr Leu Val Phe Leu Val Leu Val Ser Leu Thr
1               5                   10                  15

Gly Leu Tyr Ala Gln Val Gln Leu Gln Gln Ser Gly Pro Glu Leu Val
            20                  25                  30

Lys Pro Gly Ala Ser Leu Lys Leu Ser Cys Thr Ala Ser Gly Phe Asn
        35                  40                  45

Ile Lys Asp Thr Tyr Ile His Trp Val Lys Gln Arg Pro Glu Gln Gly
    50                  55                  60

Leu Glu Trp Ile Gly Arg Ile Tyr Pro Thr Asn Gly Tyr Thr Arg Tyr
65                  70                  75                  80

Asp Pro Lys Phe Gln Asp Lys Ala Thr Ile Thr Ala Asp Thr Ser Ser
                85                  90                  95

Asn Thr Ala Tyr Leu Gln Val Ser Arg Leu Thr Ser Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Ala Ser Val Thr Val Ser Ser Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220
```

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
            245                 250                 255

Val Phe Ile Phe Pro Pro Lys Pro Lys Asp Val Leu Thr Ile Thr Leu
        260                 265                 270

Thr Pro Lys Val Thr Cys Val Val Asp Ile Ser Lys Asp Asp Pro
    275                 280                 285

Glu Val Gln Phe Ser Trp Phe Val Asp Asp Val Glu Val His Thr Ala
290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

Ser Gly Gly Gly Gly Ser Gly Gly Gly Ser Gly Gly Gly Gly Ser
465                 470                 475                 480

Gly Gly Gly Gly Ser Gly Asn Trp Val Asn Val Ile Ser Asp Leu Lys
                485                 490                 495

Lys Ile Glu Asp Leu Ile Gln Ser Met His Ile Asp Ala Thr Leu Tyr
            500                 505                 510

Thr Glu Ser Asp Val His Pro Ser Cys Lys Val Thr Ala Met Lys Cys
        515                 520                 525

Phe Leu Leu Glu Leu Gln Val Ile Ser Leu Glu Ser Gly Asp Ala Ser
530                 535                 540

Ile His Asp Thr Val Glu Asn Leu Ile Ile Leu Ala Asn Asn Ser Leu
545                 550                 555                 560

Ser Ser Asn Gly Asn Val Thr Glu Ser Gly Cys Lys Glu Cys Glu Glu
                565                 570                 575

Leu Glu Glu Lys Asn Ile Lys Glu Phe Leu Gln Ser Phe Val His Ile
            580                 585                 590

Val Gln Met Phe Ile Asn Thr Ser
        595                 600

<210> SEQ ID NO 21
<211> LENGTH: 578
<212> TYPE: PRT
<213> ORGANISM: Artificial Sequence
<220> FEATURE:
<223> OTHER INFORMATION: IL15-anti HER2Neu Heavy chain

<400> SEQUENCE: 21

Met Ala Arg Ser Val Thr Leu Val Phe Leu Val Leu Val Ser Leu Thr
1               5                   10                  15

Gly Leu Tyr Ala Gln Val Gln Leu Gln Gln Ser Gly Pro Glu Leu Val
            20                  25                  30

Lys Pro Gly Ala Ser Leu Lys Leu Ser Cys Thr Ala Ser Gly Phe Asn
        35                  40                  45

Ile Lys Asp Thr Tyr Ile His Trp Val Lys Gln Arg Pro Glu Gln Gly
    50                  55                  60

Leu Glu Trp Ile Gly Arg Ile Tyr Pro Thr Asn Gly Tyr Thr Arg Tyr
65                  70                  75                  80

Asp Pro Lys Phe Gln Asp Lys Ala Thr Ile Thr Ala Asp Thr Ser Ser
                85                  90                  95

Asn Thr Ala Tyr Leu Gln Val Ser Arg Leu Thr Ser Glu Asp Thr Ala
            100                 105                 110

Val Tyr Tyr Cys Ser Arg Trp Gly Gly Asp Gly Phe Tyr Ala Met Asp
        115                 120                 125

Tyr Trp Gly Gln Gly Ala Ser Val Thr Val Ser Ser Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
210                 215                 220

Ala His Pro Ala Ser Ser Thr Lys Val Asp Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp

```
            405                 410                 415
Thr Asp Gly Ser Tyr Phe Val Tyr Ser Lys Leu Asn Val Gln Lys Ser
        420                 425                 430
Asn Trp Glu Ala Gly Asn Thr Phe Thr Cys Ser Val Leu His Glu Gly
            435                 440                 445
Leu His Asn His His Thr Glu Lys Ser Leu Ser His Ser Pro Gly Lys
        450                 455                 460
Asn Trp Val Asn Val Ile Ser Asp Leu Lys Lys Ile Glu Asp Leu Ile
465                 470                 475                 480
Gln Ser Met His Ile Asp Ala Thr Leu Tyr Thr Glu Ser Asp Val His
            485                 490                 495
Pro Ser Cys Lys Val Thr Ala Met Lys Cys Phe Leu Leu Glu Leu Gln
            500                 505                 510
Val Ile Ser Leu Glu Ser Gly Asp Ala Ser Ile His Asp Thr Val Glu
        515                 520                 525
Asn Leu Ile Ile Leu Ala Asn Asn Ser Leu Ser Ser Asn Gly Asn Val
        530                 535                 540
Thr Glu Ser Gly Cys Lys Glu Cys Glu Glu Leu Glu Glu Lys Asn Ile
545                 550                 555                 560
Lys Glu Phe Leu Gln Ser Phe Val His Ile Val Gln Met Phe Ile Asn
            565                 570                 575
Thr Ser

<210> SEQ ID NO 22
<211> LENGTH: 697
<212> TYPE: PRT
<213> ORGANISM: Artificial Sequence
<220> FEATURE:
<223> OTHER INFORMATION: ELI-L22-anti HER2Neu Heavy Chain

<400> SEQUENCE: 22

Met Ala Arg Ser Val Thr Leu Val Phe Leu Val Leu Val Ser Leu Thr
1               5                   10                  15
Gly Leu Tyr Ala Gln Val Gln Leu Gln Gln Ser Gly Pro Glu Leu Val
            20                  25                  30
Lys Pro Gly Ala Ser Leu Lys Leu Ser Cys Thr Ala Ser Gly Phe Asn
        35                  40                  45
Ile Lys Asp Thr Tyr Ile His Trp Val Lys Gln Arg Pro Glu Gln Gly
    50                  55                  60
Leu Glu Trp Ile Gly Arg Ile Tyr Pro Thr Asn Gly Tyr Thr Arg Tyr
65                  70                  75                  80
Asp Pro Lys Phe Gln Asp Lys Ala Thr Ile Thr Ala Asp Thr Ser Ser
            85                  90                  95
Asn Thr Ala Tyr Leu Gln Val Ser Arg Leu Thr Ser Glu Asp Thr Ala
            100                 105                 110
Val Tyr Tyr Cys Ser Arg Trp Gly Gly Asp Gly Phe Tyr Ala Met Asp
            115                 120                 125
Tyr Trp Gly Gln Gly Ala Ser Val Thr Val Ser Ser Ala Lys Thr Thr
        130                 135                 140
Pro Pro Ser Val Tyr Pro Leu Ala Pro Gly Ser Ala Ala Gln Thr Asn
145                 150                 155                 160
Ser Met Val Thr Leu Gly Cys Leu Val Lys Gly Tyr Phe Pro Glu Pro
            165                 170                 175
Val Thr Val Thr Trp Asn Ser Gly Ser Leu Ser Ser Gly Val His Thr
            180                 185                 190
```

```
Phe Pro Ala Val Leu Gln Ser Asp Leu Tyr Thr Leu Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
                260                 265                 270

Thr Pro Lys Val Thr Cys Val Val Asp Ile Ser Lys Asp Asp Pro
            275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
    450                 455                 460

Ser Gly Gly Gly Gly Ser Gly Gly Gly Ser Gly Gly Gly Gly Ser
465                 470                 475                 480

Gly Gly Gly Gly Ser Gly Ile Thr Cys Pro Pro Pro Met Ser Val Glu
                485                 490                 495

His Ala Asp Ile Trp Val Lys Ser Tyr Ser Leu Tyr Ser Arg Glu Arg
            500                 505                 510

Tyr Ile Cys Asn Ser Gly Phe Lys Arg Lys Ala Gly Thr Ser Ser Leu
        515                 520                 525

Thr Glu Cys Val Leu Asn Lys Ala Thr Asn Val Ala His Trp Thr Thr
    530                 535                 540

Pro Ser Leu Lys Cys Ile Arg Asp Pro Ala Leu Val His Gln Arg Pro
545                 550                 555                 560

Ala Pro Pro Ser Gly Gly Ser Gly Gly Gly Gly Ser Gly Gly Gly Ser
                565                 570                 575

Gly Gly Gly Gly Ser Gly Gly Asn Trp Val Asn Val Ile Ser Asp Leu
            580                 585                 590

Lys Lys Ile Glu Asp Leu Ile Gln Ser Met His Ile Asp Ala Thr Leu
        595                 600                 605
```

```
Tyr Thr Glu Ser Asp Val His Pro Ser Cys Lys Val Thr Ala Met Lys
                610                 615                 620
Cys Phe Leu Leu Glu Leu Gln Val Ile Ser Leu Glu Ser Gly Asp Ala
625                 630                 635                 640
Ser Ile His Asp Thr Val Glu Asn Leu Ile Ile Leu Ala Asn Asn Ser
                645                 650                 655
Leu Ser Ser Asn Gly Asn Val Thr Glu Ser Gly Cys Lys Glu Cys Glu
                660                 665                 670
Glu Leu Glu Glu Lys Asn Ile Lys Glu Phe Leu Gln Ser Phe Val His
                675                 680                 685
Ile Val Gln Met Phe Ile Asn Thr Ser
                690                 695
```

<210> SEQ ID NO 23
<211> LENGTH: 675
<212> TYPE: PRT
<213> ORGANISM: Artificial Sequence
<220> FEATURE:
<223> OTHER INFORMATION: RLI-anti HER2Neu Heavy chain

<400> SEQUENCE: 23

```
Met Ala Arg Ser Val Thr Leu Val Phe Leu Val Leu Val Ser Leu Thr
1               5                   10                  15
Gly Leu Tyr Ala Gln Val Gln Leu Gln Gln Ser Gly Pro Glu Leu Val
                20                  25                  30
Lys Pro Gly Ala Ser Leu Lys Leu Ser Cys Thr Ala Ser Gly Phe Asn
                35                  40                  45
Ile Lys Asp Thr Tyr Ile His Trp Val Lys Gln Arg Pro Glu Gln Gly
50                  55                  60
Leu Glu Trp Ile Gly Arg Ile Tyr Pro Thr Asn Gly Tyr Thr Arg Tyr
65                  70                  75                  80
Asp Pro Lys Phe Gln Asp Lys Ala Thr Ile Thr Ala Asp Thr Ser Ser
                85                  90                  95
Asn Thr Ala Tyr Leu Gln Val Ser Arg Leu Thr Ser Glu Asp Thr Ala
                100                 105                 110
Val Tyr Tyr Cys Ser Arg Trp Gly Gly Asp Gly Phe Tyr Ala Met Asp
                115                 120                 125
Tyr Trp Gly Gln Gly Ala Ser Val Thr Val Ser Ser Ala Lys Thr Thr
130                 135                 140
Pro Pro Ser Val Tyr Pro Leu Ala Pro Gly Ser Ala Ala Gln Thr Asn
145                 150                 155                 160
Ser Met Val Thr Leu Gly Cys Leu Val Lys Gly Tyr Phe Pro Glu Pro
                165                 170                 175
Val Thr Val Thr Trp Asn Ser Gly Ser Leu Ser Ser Gly Val His Thr
                180                 185                 190
Phe Pro Ala Val Leu Gln Ser Asp Leu Tyr Thr Leu Ser Ser Ser Val
                195                 200                 205
Thr Val Pro Ser Ser Thr Trp Pro Ser Glu Thr Val Thr Cys Asn Val
                210                 215                 220
Ala His Pro Ala Ser Ser Thr Lys Val Asp Lys Lys Ile Val Pro Arg
225                 230                 235                 240
Asp Cys Gly Cys Lys Pro Cys Ile Cys Thr Val Pro Glu Val Ser Ser
                245                 250                 255
Val Phe Ile Phe Pro Pro Lys Pro Lys Asp Val Leu Thr Ile Thr Leu
                260                 265                 270
```

-continued

```
Thr Pro Lys Val Thr Cys Val Val Asp Ile Ser Lys Asp Asp Pro
        275                 280                 285

Glu Val Gln Phe Ser Trp Phe Val Asp Asp Val Glu Val His Thr Ala
290                 295                 300

Gln Thr Gln Pro Arg Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
                340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asp
                405                 410                 415

Thr Asp Gly Ser Tyr Phe Val Tyr Ser Lys Leu Asn Val Gln Lys Ser
                420                 425                 430

Asn Trp Glu Ala Gly Asn Thr Phe Thr Cys Ser Val Leu His Glu Gly
        435                 440                 445

Leu His Asn His His Thr Glu Lys Ser Leu Ser His Ser Pro Gly Lys
        450                 455                 460

Ile Thr Cys Pro Pro Met Ser Val Glu His Ala Asp Ile Trp Val
465                 470                 475                 480

Lys Ser Tyr Ser Leu Tyr Ser Arg Glu Arg Tyr Ile Cys Asn Ser Gly
                485                 490                 495

Phe Lys Arg Lys Ala Gly Thr Ser Ser Leu Thr Glu Cys Val Leu Asn
                500                 505                 510

Lys Ala Thr Asn Val Ala His Trp Thr Thr Pro Ser Leu Lys Cys Ile
        515                 520                 525

Arg Asp Pro Ala Leu Val His Gln Arg Pro Ala Pro Pro Ser Gly Gly
530                 535                 540

Ser Gly Gly Gly Gly Ser Gly Gly Gly Ser Gly Gly Gly Gly Ser Gly
545                 550                 555                 560

Gly Asn Trp Val Asn Val Ile Ser Asp Leu Lys Lys Ile Glu Asp Leu
                565                 570                 575

Ile Gln Ser Met His Ile Asp Ala Thr Leu Tyr Thr Glu Ser Asp Val
                580                 585                 590

His Pro Ser Cys Lys Val Thr Ala Met Lys Cys Phe Leu Leu Glu Leu
        595                 600                 605

Gln Val Ile Ser Leu Glu Ser Gly Asp Ala Ser Ile His Asp Thr Val
610                 615                 620

Glu Asn Leu Ile Ile Leu Ala Asn Asn Ser Leu Ser Ser Asn Gly Asn
625                 630                 635                 640

Val Thr Glu Ser Gly Cys Lys Glu Cys Glu Glu Leu Glu Glu Lys Asn
                645                 650                 655

Ile Lys Glu Phe Leu Gln Ser Phe Val His Ile Val Gln Met Phe Ile
                660                 665                 670

Asn Thr Ser
675
```

<210> SEQ ID NO 24
<211> LENGTH: 427
<212> TYPE: PRT
<213> ORGANISM: Artificial Sequence
<220> FEATURE:
<223> OTHER INFORMATION: IL15-L22-ScFv fragment HER2Neu

<400> SEQUENCE: 24

```
Met Ala Arg Ser Val Thr Leu Val Phe Leu Val Leu Val Ser Leu Thr
1               5                   10                  15

Gly Leu Tyr Ala Asp Ile Val Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Leu Lys Arg
        115                 120                 125

Ala Thr Pro Ser His Asn Ser His Gln Val Pro Ser Ala Gly Gly Pro
    130                 135                 140

Thr Ala Asn Ser Gly Glu Val Lys Leu Val Glu Ser Gly Gly Gly Leu
145                 150                 155                 160

Val Gln Pro Gly Gly Ser Leu Arg Leu Ser Cys Ala Thr Ser Gly Phe
                165                 170                 175

Asn Ile Lys Asp Thr Tyr Ile His Trp Val Arg Gln Ala Pro Gly Lys
            180                 185                 190

Gly Leu Glu Trp Val Ala Arg Ile Tyr Pro Thr Asn Gly Tyr Thr Arg
        195                 200                 205

Tyr Ala Asp Ser Val Lys Gly Arg Phe Thr Ile Ser Ala Asp Thr Ser
    210                 215                 220

Lys Asn Thr Ala Tyr Leu Gln Met Asn Ser Leu Arg Ala Glu Asp Thr
225                 230                 235                 240

Ala Val Tyr Tyr Cys Ser Arg Trp Gly Gly Asp Gly Phe Tyr Ala Met
                245                 250                 255

Asp Tyr Trp Gly Gln Gly Thr Thr Val Thr Val Ser Ser Gly Gly Gly
            260                 265                 270

Gly Ser Gly Gly Gly Gly Ser Gly Gly Gly Ser Gly Gly Gly Gly
        275                 280                 285

Ser Gly Asn Trp Val Asn Val Ile Ser Asp Leu Lys Lys Ile Glu Asp
    290                 295                 300

Leu Ile Gln Ser Met His Ile Asp Ala Thr Leu Tyr Thr Glu Ser Asp
305                 310                 315                 320

Val His Pro Ser Cys Lys Val Thr Ala Met Lys Cys Phe Leu Leu Glu
                325                 330                 335

Leu Gln Val Ile Ser Leu Glu Ser Gly Asp Ala Ser Ile His Asp Thr
            340                 345                 350

Val Glu Asn Leu Ile Ile Leu Ala Asn Asn Ser Leu Ser Ser Asn Gly
        355                 360                 365

Asn Val Thr Glu Ser Gly Cys Lys Glu Cys Glu Glu Leu Glu Glu Lys
```

```
            370                 375                 380
Asn Ile Lys Glu Phe Leu Gln Ser Phe Val His Ile Val Gln Met Phe
385                 390                 395                 400

Ile Asn Thr Ser Glu Glu Lys Asn Ile Lys Glu Phe Leu Gln Ser Phe
                405                 410                 415

Val His Ile Val Gln Met Phe Ile Asn Thr Ser
            420                 425

<210> SEQ ID NO 25
<211> LENGTH: 405
<212> TYPE: PRT
<213> ORGANISM: Artificial Sequence
<220> FEATURE:
<223> OTHER INFORMATION: IL15-ScFv fragment HER2Neu

<400> SEQUENCE: 25

Met Ala Arg Ser Val Thr Leu Val Phe Leu Val Leu Val Ser Leu Thr
1               5                   10                  15

Gly Leu Tyr Ala Asp Ile Val Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Leu Lys Arg
        115                 120                 125

Ala Thr Pro Ser His Asn Ser His Gln Val Pro Ser Ala Gly Gly Pro
    130                 135                 140

Thr Ala Asn Ser Gly Glu Val Lys Leu Val Glu Ser Gly Gly Gly Leu
145                 150                 155                 160

Val Gln Pro Gly Gly Ser Leu Arg Leu Ser Cys Ala Thr Ser Gly Phe
                165                 170                 175

Asn Ile Lys Asp Thr Tyr Ile His Trp Val Arg Gln Ala Pro Gly Lys
            180                 185                 190

Gly Leu Glu Trp Val Ala Arg Ile Tyr Pro Thr Asn Gly Tyr Thr Arg
        195                 200                 205

Tyr Ala Asp Ser Val Lys Gly Arg Phe Thr Ile Ser Ala Asp Thr Ser
    210                 215                 220

Lys Asn Thr Ala Tyr Leu Gln Met Asn Ser Leu Arg Ala Glu Asp Thr
225                 230                 235                 240

Ala Val Tyr Tyr Cys Ser Arg Trp Gly Gly Asp Gly Phe Tyr Ala Met
                245                 250                 255

Asp Tyr Trp Gly Gln Gly Thr Thr Val Thr Val Ser Asn Trp Val Asn
            260                 265                 270

Val Ile Ser Asp Leu Lys Lys Ile Glu Asp Leu Ile Gln Ser Met His
        275                 280                 285

Ile Asp Ala Thr Leu Tyr Thr Glu Ser Asp Val His Pro Ser Cys Lys
    290                 295                 300

Val Thr Ala Met Lys Cys Phe Leu Leu Glu Leu Gln Val Ile Ser Leu
```

```
                 305                 310                 315                 320
        Glu Ser Gly Asp Ala Ser Ile His Asp Thr Val Glu Asn Leu Ile Ile
                        325                 330                 335

Leu Ala Asn Asn Ser Leu Ser Ser Asn Gly Asn Val Thr Glu Ser Gly
                        340                 345                 350

Cys Lys Glu Cys Glu Glu Leu Glu Glu Lys Asn Ile Lys Glu Phe Leu
                        355                 360                 365

Gln Ser Phe Val His Ile Val Gln Met Phe Ile Asn Thr Ser Glu Glu
                        370                 375                 380

Lys Asn Ile Lys Glu Phe Leu Gln Ser Phe Val His Ile Val Gln Met
        385                 390                 395                 400

Phe Ile Asn Thr Ser
                        405

<210> SEQ ID NO 26
<211> LENGTH: 501
<212> TYPE: PRT
<213> ORGANISM: Artificial Sequence
<220> FEATURE:
<223> OTHER INFORMATION: RLI-L22-ScFV fragment HER2Neu

<400> SEQUENCE: 26

Met Ala Arg Ser Val Thr Leu Val Phe Leu Val Leu Val Ser Leu Thr
        1               5                   10                  15

Gly Leu Tyr Ala Asp Ile Val Met Thr Gln Ser Pro Ser Ser Leu Ser
                        20                  25                  30

Ala Ser Val Gly Asp Arg Val Thr Ile Thr Cys Arg Ala Ser Gln Asp
                        35                  40                  45

Val Asn Thr Ala Val Ala Trp Tyr Gln Gln Lys Pro Gly Lys Ala Pro
                        50                  55                  60

Lys Leu Leu Ile Tyr Ser Ala Ser Phe Leu Tyr Ser Gly Val Pro Ser
        65                  70                  75                  80

Arg Phe Ser Gly Ser Arg Ser Gly Thr Asp Phe Thr Leu Thr Ile Ser
                        85                  90                  95

Ser Leu Gln Pro Glu Asp Phe Ala Thr Tyr Tyr Cys Gln Gln His Tyr
                        100                 105                 110

Thr Thr Pro Pro Thr Phe Gly Gln Gly Thr Lys Val Glu Leu Lys Arg
                        115                 120                 125

Ala Thr Pro Ser His Asn Ser His Gln Val Pro Ser Ala Gly Gly Pro
                        130                 135                 140

Thr Ala Asn Ser Gly Glu Val Lys Leu Val Glu Ser Gly Gly Gly Leu
        145                 150                 155                 160

Val Gln Pro Gly Gly Ser Leu Arg Leu Ser Cys Ala Thr Ser Gly Phe
                        165                 170                 175

Asn Ile Lys Asp Thr Tyr Ile His Trp Val Arg Gln Ala Pro Gly Lys
                        180                 185                 190

Gly Leu Glu Trp Val Ala Arg Ile Tyr Pro Thr Asn Gly Tyr Thr Arg
                        195                 200                 205

Tyr Ala Asp Ser Val Lys Gly Arg Phe Thr Ile Ser Ala Asp Thr Ser
                        210                 215                 220

Lys Asn Thr Ala Tyr Leu Gln Met Asn Ser Leu Arg Ala Glu Asp Thr
        225                 230                 235                 240

Ala Val Tyr Tyr Cys Ser Arg Trp Gly Gly Asp Gly Phe Tyr Ala Met
                        245                 250                 255

Asp Tyr Trp Gly Gln Gly Thr Thr Val Thr Val Ser Ser Gly Gly Gly
```

```
            260                 265                 270
Gly Ser Gly Gly Gly Ser Gly Gly Gly Ser Gly Gly Gly
            275                 280                 285

Ser Gly Ile Thr Cys Pro Pro Met Ser Val Glu His Ala Asp Ile
            290                 295                 300

Trp Val Lys Ser Tyr Ser Leu Tyr Ser Arg Glu Arg Tyr Ile Cys Asn
305                 310                 315                 320

Ser Gly Phe Lys Arg Lys Ala Gly Thr Ser Ser Leu Thr Glu Cys Val
                325                 330                 335

Leu Asn Lys Ala Thr Asn Val Ala His Trp Thr Thr Pro Ser Leu Lys
                340                 345                 350

Cys Ile Arg Asp Pro Ala Leu Val His Gln Arg Pro Ala Pro Pro Ser
                355                 360                 365

Gly Gly Ser Gly Gly Gly Ser Gly Gly Gly Ser Gly Gly Gly Gly
            370                 375                 380

Ser Gly Gly Asn Trp Val Asn Val Ile Ser Asp Leu Lys Lys Ile Glu
385                 390                 395                 400

Asp Leu Ile Gln Ser Met His Ile Asp Ala Thr Leu Tyr Thr Glu Ser
                405                 410                 415

Asp Val His Pro Ser Cys Lys Val Thr Ala Met Lys Cys Phe Leu Leu
                420                 425                 430

Glu Leu Gln Val Ile Ser Leu Glu Ser Gly Asp Ala Ser Ile His Asp
                435                 440                 445

Thr Val Glu Asn Leu Ile Ile Leu Ala Asn Asn Ser Leu Ser Ser Asn
450                 455                 460

Gly Asn Val Thr Glu Ser Gly Cys Lys Glu Cys Glu Glu Leu Glu Glu
465                 470                 475                 480

Lys Asn Ile Lys Glu Phe Leu Gln Ser Phe Val His Ile Val Gln Met
                485                 490                 495

Phe Ile Asn Thr Ser
            500

<210> SEQ ID NO 27
<211> LENGTH: 479
<212> TYPE: PRT
<213> ORGANISM: Artificial Sequence
<220> FEATURE:
<223> OTHER INFORMATION: RLI-ScFv fragment HER2Neu frgament

<400> SEQUENCE: 27

Met Ala Arg Ser Val Thr Leu Val Phe Leu Val Leu Val Ser Leu Thr
1               5                   10                  15

Gly Leu Tyr Ala Asp Ile Val Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
        50                  55                  60

Lys Leu Leu Ile Tyr Ser Ala Ser Phe Leu Tyr Ser Gly Val Pro Ser
65              70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Leu Lys Arg
```

```
            115                 120                 125
Ala Thr Pro Ser His Asn Ser His Gln Val Pro Ser Ala Gly Gly Pro
130                 135                 140

Thr Ala Asn Ser Gly Glu Val Lys Leu Val Glu Ser Gly Gly Gly Leu
145                 150                 155                 160

Val Gln Pro Gly Gly Ser Leu Arg Leu Ser Cys Ala Thr Ser Gly Phe
                165                 170                 175

Asn Ile Lys Asp Thr Tyr Ile His Trp Val Arg Gln Ala Pro Gly Lys
            180                 185                 190

Gly Leu Glu Trp Val Ala Arg Ile Tyr Pro Thr Asn Gly Tyr Thr Arg
        195                 200                 205

Tyr Ala Asp Ser Val Lys Gly Arg Phe Thr Ile Ser Ala Asp Thr Ser
210                 215                 220

Lys Asn Thr Ala Tyr Leu Gln Met Asn Ser Leu Arg Ala Glu Asp Thr
225                 230                 235                 240

Ala Val Tyr Tyr Cys Ser Arg Trp Gly Gly Asp Gly Phe Tyr Ala Met
                245                 250                 255

Asp Tyr Trp Gly Gln Gly Thr Thr Val Thr Val Ser Ile Thr Cys Pro
            260                 265                 270

Pro Pro Met Ser Val Glu His Ala Asp Ile Trp Val Lys Ser Tyr Ser
        275                 280                 285

Leu Tyr Ser Arg Glu Arg Tyr Ile Cys Asn Ser Gly Phe Lys Arg Lys
        290                 295                 300

Ala Gly Thr Ser Ser Leu Thr Glu Cys Val Leu Asn Lys Ala Thr Asn
305                 310                 315                 320

Val Ala His Trp Thr Thr Pro Ser Leu Lys Cys Ile Arg Asp Pro Ala
                325                 330                 335

Leu Val His Gln Arg Pro Ala Pro Pro Ser Gly Gly Ser Gly Gly Gly
            340                 345                 350

Gly Ser Gly Gly Gly Ser Gly Gly Gly Ser Gly Gly Asn Trp Val
        355                 360                 365

Asn Val Ile Ser Asp Leu Lys Lys Ile Glu Asp Leu Ile Gln Ser Met
            370                 375                 380

His Ile Asp Ala Thr Leu Tyr Thr Glu Ser Asp Val His Pro Ser Cys
385                 390                 395                 400

Lys Val Thr Ala Met Lys Cys Phe Leu Leu Glu Leu Gln Val Ile Ser
                405                 410                 415

Leu Glu Ser Gly Asp Ala Ser Ile His Asp Thr Val Glu Asn Leu Ile
            420                 425                 430

Ile Leu Ala Asn Asn Ser Leu Ser Ser Asn Gly Asn Val Thr Glu Ser
            435                 440                 445

Gly Cys Lys Glu Cys Glu Glu Leu Glu Glu Lys Asn Ile Lys Glu Phe
        450                 455                 460

Leu Gln Ser Phe Val His Ile Val Gln Met Phe Ile Asn Thr Ser
465                 470                 475
```